(12) United States Patent
Chodorowski-Kimmes et al.

(10) Patent No.: US 8,968,711 B2
(45) Date of Patent: Mar. 3, 2015

(54) COSMETIC OR DERMATOLOGICAL COMPOSITION COMPRISING A POLYMER BEARING JUNCTION GROUPS, AND COSMETIC TREATMENT PROCESS

(75) Inventors: Sandrine Chodorowski-Kimmes, Senlis (FR); Pascal Giustiniani, La Garenne Colombes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/679,839

(22) PCT Filed: Oct. 3, 2008

(86) PCT No.: PCT/FR2008/051795
§ 371 (c)(1),
(2), (4) Date: Jun. 7, 2010

(87) PCT Pub. No.: WO2009/053594
PCT Pub. Date: Apr. 30, 2009

(65) Prior Publication Data
US 2010/0239509 A1     Sep. 23, 2010

(30) Foreign Application Priority Data

Oct. 5, 2007  (FR) ..................................... 07 58099

(51) Int. Cl.
| | | |
|---|---|---|
| *A61K 8/85* | (2006.01) |
| *A61Q 1/04* | (2006.01) |
| *A61Q 3/00* | (2006.01) |
| *A61Q 5/00* | (2006.01) |
| *A61Q 17/04* | (2006.01) |
| *A61Q 1/06* | (2006.01) |
| *A61Q 3/02* | (2006.01) |
| *C08G 18/42* | (2006.01) |
| *C08G 18/71* | (2006.01) |
| *C08G 63/48* | (2006.01) |

(52) U.S. Cl.
CPC ... *A61K 8/85* (2013.01); *A61Q 1/04* (2013.01); *A61Q 1/06* (2013.01); *A61Q 3/02* (2013.01); *C08G 18/4208* (2013.01); *C08G 18/714* (2013.01); *C08G 63/48* (2013.01)
USPC .................. 424/59; 424/61; 424/63; 424/64; 424/70.11

(58) Field of Classification Search
None
See application file for complete search history.

(56) References Cited

U.S. PATENT DOCUMENTS

| | | | | |
|---|---|---|---|---|
| 2,915,488 | A  * | 12/1959 | Kraft et al. ................. | 528/295.5 |
| 2004/0161394 | A1 | 8/2004 | Mougin et al. | |
| 2006/0062752 | A1 * | 3/2006 | Gotou et al. ............... | 424/70.31 |
| 2006/0140702 | A1 | 6/2006 | Coffey-Dawe | |
| 2007/0264208 | A1 * | 11/2007 | Mougin et al. .................. | 424/59 |
| 2008/0069786 | A1 | 3/2008 | Rodriguez et al. | |
| 2008/0152607 | A1 | 6/2008 | Malle et al. | |
| 2009/0028807 | A1 | 1/2009 | Giustiniani et al. | |

FOREIGN PATENT DOCUMENTS

| | | |
|---|---|---|
| EP | 1 797 867 | 6/2007 |
| FR | 2 825 628 | 12/2002 |
| FR | 2 879 920 | 6/2006 |
| WO | WO 2004052963 A1 * | 6/2004 |
| WO | 2006/017203 | 2/2006 |

OTHER PUBLICATIONS

U.S. Appl. No. 12/681,473, filed Apr. 2, 2010, Malle.
Japanese Office Action issued Jul. 30, 2013, in Patent Application No. 2010-527507.

* cited by examiner

*Primary Examiner* — Susan Tran
*Assistant Examiner* — Jessica Worsham
(74) *Attorney, Agent, or Firm* — Oblon, McClelland, Maier & Neustadt, L.L.P.

(57) ABSTRACT

The present patent application relates to a cosmetic or dermatological composition comprising, in a cosmetically or dermatologically acceptable medium, a polymer comprising:
(a) a polymer backbone that may be obtained by reaction:
of a polyol comprising 3 to 6 hydroxyl groups;
of a monocarboxylic acid containing 6 to 32 carbon atoms;
of a polycarboxylic acid comprising at least two carboxylic groups COOH, and/or of a cyclic anhydride such as a polycarboxylic acid and/or of a lactone comprising at least one carboxylic group COOH; and
(b) at least one junction group linked to the said polymer backbone and capable of establishing H bonds with one or more partner junction groups, each pairing of a junction group involving at least three H (hydrogen) bonds.

The patent application also concerns a cosmetic treatment process using the said composition.

28 Claims, No Drawings

COSMETIC OR DERMATOLOGICAL COMPOSITION COMPRISING A POLYMER BEARING JUNCTION GROUPS, AND COSMETIC TREATMENT PROCESS

The present invention relates to cosmetic compositions comprising novel polymers of the polycondensate family, and also to cosmetic treatment processes using them.

Many cosmetic compositions exist for which gloss properties of the deposited film, after application to keratin materials (skin, lips or integuments), are desired. Examples that may be mentioned include lipsticks, nail varnishes or certain haircare products.

In order to obtain such a result, it is possible to combine particular starting materials, especially lanolins, with "glossy" oils, such as polybutenes, which, however, have a high viscosity; or esters of a fatty acid or a fatty alcohol with a high carbon number; or alternatively certain plant oils; or alternatively esters resulting from the partial or total esterification of a hydroxylated aliphatic compound with an aromatic acid, as described in patent application EP 1 097 699.

It is also known practice to combine lanolins with polyesters obtained by sequential reaction of castor oil with isostearic acid and then with succinic acid, as described in U.S. Pat. No. 6,342,527.

To improve the gloss of the deposited film, and also its staying power, it has also been proposed to use esters resulting from the condensation of a polyol with a carboxylic acid of "neo" type, especially in FR 2 838 049.

Mention may also be made of EP 1 457 201, which describes a composition comprising a polyester of hydroxylated carboxylic acid triglycerides and an oil of low molecular mass chosen from polybutylenes, hydrogenated polyisobutylenes, hydrogenated or non-hydrogenated polydecenes, vinylpyrrolidone copolymers, linear fatty acid esters, hydroxylated esters, esters of branched $C_{24}$-$C_{28}$ fatty alcohols or fatty acids, silicone oils and/or oils of plant origin.

Patent application EP 1 155 687 describes a process that consists in incorporating, into an oily phase formed from a cosmetically acceptable oil, an organopolysiloxane containing at least two groups capable of establishing hydrogen bonds.

However, these compositions and combinations, although they can improve the gloss, are still judged insufficient with regard to long staying power of this gloss over time. Specifically, it has been found that the staying power of this gloss over time is limited.

The aim of the present invention is to propose cosmetic compositions that contain novel polymers capable of uniting long-lasting staying power of the gloss of the composition and gloss, while at the same time obviously maintaining the required cosmetic properties.

Polymers that are capable of imparting significant gloss to a deposit, especially a film-forming deposit, while at the same time maintaining good durability over time of this gloss, are most particularly sought; this may find a particularly advantageous application in the field of lipsticks. Polymers that can also give the composition excellent staying power over time on keratin materials, especially on the lips, are also sought.

After considerable research, the Applicant has discovered, surprisingly and unexpectedly, that certain functionalized polycondensates can lead to improved performance in terms of gloss, maintenance of the said gloss and also long staying power of the film obtained, while at the same time being conveyable in the usual cosmetic media, especially the usual oily cosmetic media.

One subject of the present invention is thus a cosmetic or dermatological composition comprising, in a cosmetically or dermatologically acceptable medium, a polymer comprising:
(a) a polymer backbone that may be obtained by reacting:
  from 10% to 60% by weight, relative to the total weight of the said backbone, of at least one polyol comprising 3 to 6 hydroxyl groups;
  from 0.1% to 80% by weight, relative to the total weight of the said backbone, of at least one monocarboxylic acid containing 6 to 32 carbon atoms;
  from 5% to 60% by weight, relative to the total weight of the said backbone, of at least one polycarboxylic acid comprising at least two carboxylic groups COOH, and/or a cyclic anhydride such as a polycarboxylic acid and/or a lactone comprising at least one carboxylic group COOH; and
(b) at least one junction group linked to the said polymer backbone and capable of establishing H bonds with one or more partner junction groups, each pairing of a junction group involving at least three H (hydrogen) bonds.

Another subject of the invention is a cosmetic treatment process using the said composition.

The cosmetic compositions according to the invention show good applicability and good coverage; good adhesion to the support, whether to the nail, the hair, the eyelashes, the skin or the lips; suitable flexibility and strength of the film, which makes it possible to avoid cracking, for example in the case of varnishes or lipsticks; and also an excellent level of long-lasting gloss.

The comfort and glidance properties are also very satisfactory.

The film obtained has a rigidity and flexibility that are suitable for its use in cosmetic compositions of lipstick or foundation type, while at the same time having gloss and gloss staying power as desired.

Moreover, advantageously and surprisingly, these functionalized polycondensates are easy to convey in cosmetic oily or solvent media, especially oils, fatty alcohols and/or fatty esters, which facilitates their use in the cosmetic field, especially in lipsticks or foundations.

They show suitable solubility in various cosmetic oily media, such as plant oils, alkanes, esters, which may be short esters such as butyl or ethyl acetate, or fatty esters, fatty alcohols, silicone oils, and especially including isododecane, Parleam, isononyl isononanoate, octyldodecanol, phenyl trimethicone, $C_{12}$-$C_{15}$ alkyl benzoates and/or D5 (decamethylcyclopentasiloxane).

The functionalized polycondensates according to the invention are advantageously branched; it may be considered that this makes it possible to generate a network by entanglement of the polymer chains, and thus to obtain the desired properties, especially in terms of improved staying power, improved gloss and solubility.

The polycondensates of alkyd type forming the polymer backbone (referred to hereinbelow as POL) may be obtained by esterification/polycondensation, according to the methods known to those skilled in the art, of the constituents described below.

One of the constituents necessary for preparing these polycondensates is a compound comprising 3 to 6 hydroxyl groups (polyol), especially 3 to 4 hydroxyl groups. It is obviously possible to use a mixture of such polyols. The said polyol may especially be a linear, branched and/or cyclic, saturated or unsaturated carbon-based and especially hydrocarbon-based compound, containing 3 to 18 carbon atoms, especially 3 to 12 or even 4 to 10 carbon atoms, and 3 to 6 hydroxyl groups (OH), and also possibly comprising one or more oxygen atoms intercalated in the chain (ether function).

The said polyol is preferably a linear or branched, saturated hydrocarbon-based compound, containing 3 to 18 carbon atoms, especially 3 to 12 or even 4 to 10 carbon atoms, and 3 to 6 hydroxyl groups (OH).

It may be chosen, alone or as a mixture, from:

triols, such as 1,2,4-butanetriol, 1,2,6-hexanetriol, trimethylolethane, trimethylolpropane or glycerol;

tetraols, such as pentaerythritol (tetramethylolmethane), erythritol, diglycerol or ditrimethylolpropane;

pentols such as xylitol, hexols such as sorbitol and mannitol; or alternatively dipentaerythritol or triglycerol.

Preferably, the polyol is chosen from glycerol, pentaerythritol and sorbitol, and mixtures thereof; and better still is pentaerythritol.

The polyol, or the polyol mixture, preferably represents 10% to 60% by weight, especially 12% to 40% by weight and better still 14% to 25% by weight relative to the total weight of the polycondensate forming the polymer backbone.

Another constituent necessary for preparing these polycondensates is a monocarboxylic acid containing 6 to 32 carbon atoms. It is obviously possible to use a mixture of such monocarboxylic acids, which are especially aromatic or non-aromatic.

This monocarboxylic acid may be non-aromatic, saturated or unsaturated, linear, branched and/or cyclic, containing 6 to 32 carbon atoms, especially 8 to 28 carbon atoms and better still 10 to 20 or even 12 to 18 carbon atoms. The term "non-aromatic monocarboxylic acid" means a compound of formula RCOOH, in which R is a linear, branched and/or cyclic, saturated or unsaturated hydrocarbon-based radical, containing 5 to 31 carbon atoms, especially 7 to 27 carbon atoms and better still 9 to 19 carbon atoms, or even 11 to 17 carbon atoms. Preferably, the radical R is saturated. Better still, the said radical R is linear or branched, and preferentially of $C_5$-$C_{31}$.

The non-aromatic monocarboxylic acids may be chosen from conjugated polyunsaturated monocarboxylic acids, unconjugated monocarboxylic acids, and a mixture thereof. The unconjugated acids include saturated acids, monounsaturated acids and non-conjugated polyunsaturated acids.

This monocarboxylic acid may also be aromatic, containing 7 to 11 carbon atoms, and also optionally substituted with 1 to 3 saturated or unsaturated, linear, branched and/or cyclic alkyl radicals, containing 1 to 32 carbon atoms, especially 2 to 12 or even 3 to 8 carbon atoms. It is obviously possible to use a mixture of such aromatic monocarboxylic acids. The term "aromatic monocarboxylic acid" means a compound of formula R'COOH, in which R' is an aromatic hydrocarbon-based radical containing 6 to 10 carbon atoms, and in particular benzoic and naphthoic radicals. The said radical R' may also be substituted with 1 to 3 saturated or unsaturated, linear, branched and/or cyclic alkyl radicals, containing 1 to 32 carbon atoms and especially 2 to 12 or even 3 to 8 carbon atoms; and especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl and isooctyl.

Among the non-aromatic monocarboxylic acids that may be used, mention may be made, alone or as a mixture, of:

saturated monocarboxylic acids such as caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid and 4-cyclohexylbutyric acid;

non-aromatic unsaturated monocarboxylic acids, such as caproleic acid, obtusilic acid, undecylenic acid, dodecylenic acid, linderic acid, myristoleic acid, physeteric acid, tsuzuic acid, palmitoleic acid, oleic acid, petroselinic acid, vaccenic acid, elaidic acid, gondoic acid, gadoleic acid, erucic acid, ketoleic acid, nervonic acid, oleic acid, linoleic acid, linolenic acid, arachidonic acid, rumenic acid, eicosapentaenoic acid and docosahexaenoic acid;

conjugated acids such as stillinguic acid (10:2 2t,4c), rumenic acid (18:2, 9c,11t), conjugated linoleic acid (18:2 10t,12c), conjugated linolenic acid (18:3 9c,11t,15c), conjugated linolenic acid (18:3 6c,9c,11t) and alpha-eleostearic acid (18:3 9c,11t,13t), alone or as a mixture.

Among the aromatic monocarboxylic acids that may be used, mention may be made, alone or as a mixture, of benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid.

Preferably, a mixture of non-aromatic monocarboxylic acids and of aromatic monocarboxylic acids may be used. The proportion of each of the acids may be chosen by a person skilled in the art so as to obtain a polymer having the desired solubility. Thus, as a guide, if a polymer that is rather soluble in short esters such as ethyl or butyl acetate is desired, the non-aromatic monocarboxylic acid, or the mixture thereof, preferably represents 1% to 80% by weight, especially 5% to 50% by weight or even 8% to 40% by weight, relative to the total weight of the mixture of monocarboxylic acids, and the aromatic monocarboxylic acid, or the mixture thereof, preferably represents 20% to 99% by weight, especially 50% to 95% by weight and better still from 60% to 92% by weight, relative to the total weight of the said mixture. If a polymer that is rather soluble in cosmetic oils (for example fatty esters or alkanes) is desired, the non-aromatic monocarboxylic acid, or the mixture thereof, preferably represents 10% to 99% by weight, especially 50% to 95% by weight, or even 55% to 90% by weight, relative to the total weight of the mixture of monocarboxylic acids, and the aromatic monocarboxylic acid, or the mixture thereof, preferably represents 1% to 90% by weight, especially 5% to 50% by weight and better still from 10% to 45% by weight relative to the total weight of the said mixture.

Preferably, lauric acid, palmitic acid, stearic acid, behenic acid, 2-ethylhexanoic acid, isooctanoic acid, isononanoic acid, isostearic acid, benzoic acid, 4-tert-butylbenzoic acid, o-toluic acid, m-toluic acid, 1-naphthoic acid, caproleic acid, obtusilic acid, undecylenic acid, dodecylenic acid, linderic acid, myristoleic acid, physeteric acid, tsuzuic acid, palmitoleic acid, oleic acid, linoleic acid, linolenic acid or arachidonic acid, and mixtures thereof, may be used as monocarboxylic acid.

The monocarboxylic acid, or the mixture thereof, preferably represents 0.1% to 80% by weight, especially 0.5% to 70% by weight, or even 1% to 65% by weight, and better still 1.5% to 60% by weight, relative to the total weight of the polycondensate forming the polymer backbone.

Another constituent that is necessary for preparing the polycondensates according to the invention is a polycarboxylic acid, and/or a cyclic anhydride of such a polycarboxylic acid, and/or a lactone bearing at least one COOH group; and also mixtures thereof.

The said polycarboxylic acid may be chosen especially from linear, branched and/or cyclic, saturated or unsaturated, or even aromatic, polycarboxylic acids, containing 2 to 50, especially 2 to 40 carbon atoms, in particular 3 to 36, or even 3 to 18 and better still 4 to 12 carbon atoms, or even 5 to 10 carbon atoms; the said acid comprising at least two carboxylic groups COOH and preferably from 2 to 4 COOH groups; and possibly comprising 1 to 10 and preferably 1 to 6 identical or different heteroatoms, chosen from O, N and S; and/or possibly comprising at least one perfluoro radical chosen from —CF$_2$— (divalent) or —CF$_3$.

Preferably, the said polycarboxylic acid is saturated, linear and aliphatic and contains 2 to 36 carbon atoms, especially 3 to 18 carbon atoms or even 4 to 12 carbon atoms; or alternatively is aromatic and contains 8 to 12 carbon atoms. It preferably comprises 2 to 4 COOH groups.

The said cyclic anhydride of such a polycarboxylic acid may especially correspond to one of the following formulae:

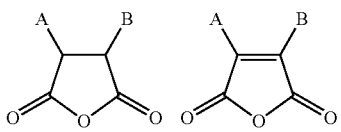

in which the groups A and B are, independently of each other:
a hydrogen atom,
a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl,
or alternatively A and B taken together form a saturated or unsaturated, or even aromatic, ring comprising in total 5 to 14, especially 5 to 10 or even 6 to 7 carbon atoms.

Preferably, A and B represent a hydrogen atom or together form an aromatic ring containing in total 6 to 10 carbon atoms.

Among the polycarboxylic acids or anhydrides thereof that may be used, mention may be made, alone or as a mixture, of:
dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid and fatty acid dimers (especially of C$_{36}$) such as the products sold under the trade names Pripol 1006, 1009, 1013 and 1017 by Uniqema,
tricarboxylic acids such as cyclohexanetricarboxylic acid, trimellitic acid, 1,2,3-benzenetricarboxylic acid and 1,3,5-benzenetricarboxylic acid,
tetracarboxylic acids such as butanetetracarboxylic acid and pyromellitic acid,
cyclic anhydrides of these acids and especially phthalic anhydride, trimellitic anhydride, maleic anhydride and succinic anhydride.

Preferably, adipic acid, phthalic anhydride and/or isophthalic acid, and better still isophthalic acid alone, may be used.

Mention may also be made of polycarboxylic acids chosen, alone or as a mixture, from:
(i) polycarboxylic acids containing a saturated or unsaturated, linear or branched chain comprising at least one heteroatom chosen from O, N and/or S, especially 1 to 10 identical or different heteroatoms, and/or comprising at least one perfluoro radical —CF$_2$— or —CF$_3$ and moreover containing at least 2 carboxylic groups COOH and especially 2 to 4 COOH groups; and/or a cyclic anhydride of such a polycarboxylic acid; and/or (ii) saturated or unsaturated, or even aromatic, heterocyclic polycarboxylic acids, comprising at least one heteroatom chosen from O, N and/or S, especially 1 to 10, or even 1 to 4, identical or different heteroatoms, and at least 2 carboxylic groups COOH and especially 2 to 4 COOH groups; and/or a cyclic anhydride of such a polycarboxylic acid; and/or (iii) sugar-based polycarboxylic acids, which may be obtained especially by oxidation of an aldose, and comprising at least 2 carboxylic groups COOH and especially 2 or 3 COOH groups; and/or a cyclic anhydride of such a polycarboxylic acid; and/or (iv) itaconic anhydride and 1,4,5,8-naphthalenetetracarboxylic acid 1,4-monoanhydride; and/or (v) polycarboxylic (including heterocyclic) amino acids, i.e. polycarboxylic acids containing a saturated or unsaturated, linear, branched and/or cyclic chain, optionally comprising at least one heteroatom chosen from O, N and/or S, especially 1 to 10 identical or different heteroatoms, and/or optionally comprising at least one perfluoro radical —CF$_2$— or —CF$_3$; and also comprising at least one primary, secondary or tertiary amine function (especially NR1R2 with R1 and R2, independently of each other, chosen from H and C$_1$-C$_{12}$ alkyl), especially 1 to 3 identical or different amine functions, and moreover containing at least 2 carboxylic groups COOH, especially 2 to 4 COOH groups; and/or a cyclic anhydride of such a polycarboxylic acid.

Mention may be made most particularly, alone or as a mixture, of the following dicarboxylic acids:
(i)
2,2'-[1,5-pentanediylbis(thio)]bis-acetic acid
6,6'-[(1,2-dioxo-1,2-ethanediyl)diimino]bis-hexanoic acid
2,2'-sulfinylbis-acetic acid
4,13-dioxo-3,5,12,14-tetraazahexadecanedioic acid
poly(ethylene glycol)disuccinate, especially of mass 250-600
poly(ethylene glycol)bis(carboxymethyl) ether, especially of mass 250-600
poly[oxy(1,2-dicarboxy-1,2-ethanediyl)], especially of DP<10
8-[(carboxymethyl)amino]-8-oxooctanoic acid
2,2'-[methylenebis(sulfonyl)]bis-acetic acid
4,4'-(1,6-hexanediyldiimino)bis[4-oxobutanoic acid]
4,9-dioxo-3,5,8,10-tetraazadodecanedioic acid
4-[(1-carboxyethyl)amino]-4-oxobutanoic acid
6-[(3-carboxy-1-oxopropyl)amino]hexanoic acid
N,N'-(1,6-dioxo-1,6-hexanediyl)bis-glycine
N,N'-(1,6-dioxo-1,6-hexanediyl)bis-phenylalanine
N,N'-(1,3-dioxo-1,3-propanediyl)-glycine
4,4'-[(1,4-dioxo-1,4-butanediyl)diimino]bis-butanoic acid
4,4'-[(1,6-dioxo-1,6-hexanediyl)diimino]bis-butanoic acid
6,6'-[1,6-hexanediylbis(iminocarbonylimino)]bis-hexanoic acid
N-benzoyl-S-(carboxymethyl)cysteine
N,N'-(2,2,3,3-tetrafluoro-1,4-dioxo-1,4-butanediyl)bis-glycine
N,N'-(2,2,3,3-tetrafluoro-1,4-dioxo-1,4-butanediyl)bis-alanine
4,4'-[(2,2,3,3-tetrafluoro-1,4-dioxo-1,4-butanoic acid
N,N'-(1,5-dioxo-1,5-pentanediyl)bis-glycine
N,N'-(1,9-dioxo-1,9-nonanediyl)bis-glycine
N,N'-(1,10-dioxo-1,10-decanediyl)bis[N-methyl]glycine
bis(3-carboxypropyl)ester of propanedioic acid
7,16-dioxo-6,8,15,17-tetraazadocosanedioic acid N-benzoyl-N-(2-carboxyethyl)glycine
[2-[(2-carboxymethyl)amino]-2-oxoethyl]benzenepropanoic acid
[2-[(2-carboxyethyl)amino]-2-oxoethyl]benzenepropanoic acid
(ii)
4,7,9,12-tetraoxapentadecanedioic acid
2,3-pyridinedicarboxylic acid
4-pyranone-2,6-dicarboxylic acid
2,5-pyrazinedicarboxylic acid
2,5-pyridinedicarboxylic acid
2,3-benzofurandicarboxylic acid
7-oxabicyclo[2.2.1]heptane-2,3-dicarboxylic acid
3,4-pyridinedicarboxylic acid
2,4-pyridinedicarboxylic acid
3,5-pyridinedicarboxylic acid
2,6-pyridinedicarboxylic acid
1H-imidazole-4,5-dicarboxylic acid
2,3-quinolinedicarboxylic acid
6,6,7,7-tetrafluoro-3-oxabicyclo[3.2.0]heptane-2,4-dicarboxylic acid
2,6-pyrazinedicarboxylic acid
2,6-dimethyl-3,5-pyridinedicarboxylic acid
1-phenyl-1H-pyrazole-3,4-dicarboxylic acid
2,5-furandicarboxylic acid
3,4-furandicarboxylic acid
1,2,5-thiadiazole-3,4-dicarboxylic acid
1,4-dihydro-1,2,4,5-tetrazine-3,6-dicarboxylic acid
2,3-furandicarboxylic acid
3,4-thiophenedicarboxylic acid
1H-1,2,3-triazole-4,5-dicarboxylic acid
2-methylimidazole-4,5-dicarboxylic acid
2,4-quinolinedicarboxylic acid
naphtho[2,1-b]furan-1,2-dicarboxylic acid
3,4-quinolinedicarboxylic acid
7-oxabicyclo[2.2.1]hept-5-ene-2,3-dicarboxylic acid
2,3-quinoxalinedicarboxylic acid
1,4-piperazinedicarboxylic acid
2,5-dimethyl-3,4-furandicarboxylic acid
tetrahydro-2,5-thiophenedicarboxylic acid
4-phenyl-3,5-pyridinedicarboxylic acid
thieno[3,2-b]thiophene-2,5-dicarboxylic acid
3-methyl-2,4-thiophenedicarboxylic acid
naphthostyril-5,6-dicarboxylic acid
3-phenyl-2,4-quinolinedicarboxylic acid
3,4-dimethyl-2,5-dicarboxythiophene
3,4-diphenyl-2,5-thiophenedicarboxylic acid
2,5-diphenyl-3,4-furandicarboxylic acid
7-oxo-7H-benzimidazo[2,1-a]benz[de]isoquinoline-3,4-dicarboxylic acid
2,3-dihydro-1,3-dioxo-1H-benz[de]isoquinoline-6,7-dicarboxylic acid
3,4-bis(phenylmethoxy)-2,5-furandicarboxylic acid
4,4'-bibenzoic acid-2,2'-sulfone
2,7-diphenyl-m-anthrazoline-4,5-dicarboxylic acid
2,4-pyrimidinedicarboxylic acid
2-phenyl-4,5-thiazoledicarboxylic acid
6-phenyl-2,3-pyridinedicarboxylic acid
5,6-dimethyl-2,3-pyrazinedicarboxylic acid
3,7-dibenzothiophenedicarboxylic acid
9-oxo-9H-xanthene-1,7-dicarboxylic acid
2-(1,1-dimethylethyl)-H-imidazole-4,5-dicarboxylic acid
6,7-quinolinedicarboxylic acid
6-methyl-2,3-pyridinedicarboxylic acid
4,5-pyrimidinedicarboxylic acid
2-methyl-3,4-furandicarboxylic acid
1,2-indolizinedicarboxylic acid
2,8-dibenzothiophenedicarboxylic acid
3,6-pyridazinedicarboxylic acid
1,10-phenanthroline-2,9-dicarboxylic acid
1,4,5,6-tetrahydro-5,6-dioxo-2,3-pyrazinedicarboxylic acid
3,4-dimethoxy-2,5-furandicarboxylic acid
2-ethyl-4,5-imidazoledicarboxylic acid
2-propyl-1H-imidazole-4,5-dicarboxylic acid
4-phenyl-2,5-pyridinedicarboxylic acid
4,5-pyridazinedicarboxylic acid
1,4,5,8-tetrahydro-1,4:5,8-diepoxynaphthalene-4a,8a-dicarboxylic acid
5,5-dioxide-2,8-dibenzothiophenedicarboxylic acid
pyrazolo[1,5-a]pyridine-2,3-dicarboxylic acid
2,3-dihydro-1H-pyrrolizine-1,7-dicarboxylic acid
6-methyl-2,4,5-pyridinetricarboxylic acid
pyrrolo[2,1,5-cd]indolizine-5,6-dicarboxylic acid
3,4-bis(2,2,3,3,4,4,4-heptafluorobutyl)-1H-pyrrole-2,5-dicarboxylic acid
6,7,9,10,17,18,20,21-octahydrodibenzo[b,k]-[1,4,7,10,13,16]hexaoxacyclooctadecin-2,14-dicarboxylic acid
6,7,9,10,17,18,20,21-octahydrodibenzo[b,k]-[1,4,7,10,13,16]hexaoxacyclooctadecin-2,13-dicarboxylic acid
2-methyl-3,4-quinolinedicarboxylic acid
4,7-quinolinedicarboxylic acid
3,5-isoxazoledicarboxylic acid
2-(trifluoromethyl)-3,4-furandicarboxylic acid
5-(trifluoromethyl)-2,4-furandicarboxylic acid
6-methyl-2,4-quinolinedicarboxylic acid
5-oxo-1,2-pyrrolidinedicarboxylic acid
5-ethyl-2,3-pyridinedicarboxylic acid
1,2-dihydro-2-oxo-3,4-quinolinedicarboxylic acid
4,6-phenoxathiindicarboxylic acid
10,10-dioxide 1,9-phenoxathiindicarboxylic acid
3,4-dihydro-2H-1,4-thiazine-3,5-dicarboxylic acid
2,7-di(tert-butyl)-9,9-dimethyl-4,5-xanthenedicarboxylic acid
6-methyl-2,3-quinoxalinedicarboxylic acid
3,7-quinolinedicarboxylic acid
2,5-quinolinedicarboxylic acid
2-methyl-6-phenyl-3,4-pyridinedicarboxylic acid
3,4-dimethylthieno[2,3-b]thiophene-2,5-dicarboxylic acid
3,4-dimethoxythiophene-2,5-dicarboxylic acid
5-methyl-3,4-isoxazoledicarboxylic acid
2,6-bis(aminocarbonyl)-3,5-pyridinedicarboxylic acid
3,5-bis(aminocarbonyl)-2,6-pyrazinedicarboxylic acid
2,3-pyridinedicarboxylic acid
6-(1,1-dimethylethyl)-2-ethyl-3,4-pyridinedicarboxylic acid
3-methyl-5-phenyl-2,4-thiophenedicarboxylic acid
1,2-dihydro-2-oxo-6-phenyl-3,5-pyridinedicarboxylic acid
8-methyl-2,4-quinolinedicarboxylic acid
4-ethyl-2,6-dimethyl-3,5-pyridinedicarboxylic acid
5-(phenoxymethyl)-2,4-furandicarboxylic acid
5-(acetylamino)-3-methyl-2,4-thiophenedicarboxylic acid
2-(4-heptylphenyl)-4,8-quinolinedicarboxylic acid
2,8-bis(4-heptylphenyl)pyrido[3,2-g]quinoline-4,6-dicarboxylic acid
1,2,3,4,6,7,8,9-octahydro-2,8-dioxopyrido[3,2]-quinoline-3,7-dicarboxylic acid
2,8-dimethylpyrido[3,2-g]quinoline-3,7-dicarboxylic acid
5,6-quinolinedicarboxylic acid
6-ethyl-2-methylcinchomeronic acid
2-methyl-6-propylcinchomeronic acid
6-isopropyl-2-methylcinchomeronic acid
6-tert-butyl-2-methylcinchomeronic acid
1,4-dimethyl-7-oxabicyclo[2.2.1]heptane-2,3-dicarboxylic acid
1,2-dihydro-2-oxo-3,8-quinolinedicarboxylic acid 1,2-dihydro-2-oxo-3,6-quinolinedicarboxylic acid
1,2-dihydro-2-oxo-3,7-quinolinedicarboxylic acid
3,7-dimethyl-2,8-diphenylpyrido[3,2-g]quinoline-4,6-dicarboxylic acid
8-methyl-2,3-quinolinedicarboxylic acid
3-[[(1,1-dimethylethyl)amino]sulfonyl]-2,5-thiophenedicarboxylic acid
4-(acetylamino)-2,3-thiophenedicarboxylic acid
2,5-pyridinedicarboxylic acid
2,6-pyridinedicarboxylic acid
2,4-thiophenedicarboxylic acid
2,5-thiophenedicarboxylic acid
1,4-pyran-2,6-dicarboxylic acid
(iii)
ribaric acid
glucaric acid
xylaric acid
arabinaric acid
mannaric acid
idaric acid
altraric acid
L-glucaric acid
L-arabinaric acid
allaric acid
galactaric acid
meso-tartaric acid
D-glucaric acid
L-idaric acid
hexaric acid
2,3-dihydroxybutanedioic acid
D-tartaric acid
D,L-tartaric acid
D-glucaric acid
tartaric acid
tetrahydroxysuccinic acid
2-carboxy-2,3-dideoxy-D-manno-2-octulopyranosonic acid
methyl-3-deoxy-D-arabino-2-heptulopyranosaric acid
D-lyxo-2-heptulopyranosaric acid
2,6-anhydro-L-glycero-L-galactoheptaric acid
(iv)
1,4,5,8-naphthalenetetracarboxylic acid 1,4-monoanhydride
itaconic anhydride
(v)
1,4-dihydro-4-oxo-2,6-pyridinedicarboxylic acid
2,6-piperidinedicarboxylic acid
1H-pyrrole-3,4-dicarboxylic acid
4-amino-2,6-dicarboxylic acid
1-methyl-1H-pyrazole-3,4-dicarboxylic acid
2,3-piperidinedicarboxylic acid
1-methyl-1H-imidazole-4,5-dicarboxylic acid
2,4-thiazolidinedicarboxylic acid
1-(phenylmethyl)-1H-imidazole-4,5-dicarboxylic acid
5-amino-6-oxo-2,3-piperidinedicarboxylic acid
5-amino-6-oxo-2,4-piperidinedicarboxylic acid
5-amino-6-oxo-2,3-piperidinedicarboxylic acid
5-amino-6-oxo[2S-(2α,4β,5α)]-2,4-piperidinedicarboxylic acid
(2S,4R)-2,4-pyrrolidinedicarboxylic acid
(2S-cis)-2,4-pyrrolidinedicarboxylic acid
2-amino-1H-imidazole-4,5-dicarboxylic acid
2,5-pyrrolidinedicarboxylic acid
4-amino-3,5-isothiazoledicarboxylic acid
1-methyl-1H-pyrazole-3,5-dicarboxylic acid
7-(diethylamino)-2-oxo-2H-1-benzopyran-3,4-dicarboxylic acid
3,4-diethyl-1H-pyrrole-2,5-dicarboxylic acid
1-phenyl-1H-pyrrole-3,4-dicarboxylic acid
cis-2,3-piperazinedicarboxylic acid
2,3-piperazinedicarboxylic acid
2,5-piperazinedicarboxylic acid
2,6-piperazinedicarboxylic acid
2-amino-3,5-pyridinedicarboxylic acid
2-methylpyrrole-3,4-dicarboxylic acid
4-(methylamino)-2,6-pyridinedicarboxylic acid
2-amino-6-methyl-3,4-pyridinedicarboxylic acid
5-amino-2-methyl-3,4-pyridinedicarboxylic acid
2-amino-6-methyl-3,5-pyridinedicarboxylic acid
2,5-dimethylpyrrole-3,4-dicarboxylic acid
2,5-dimethylpyrrole-3,4-dicarboxylic acid
2-amino-6-hydroxy-3,5-pyridinedicarboxylic acid
2,4-pyrrolidinedicarboxylic acid
1H-indole-2,4-dicarboxylic acid
1H-indole-2,6-dicarboxylic acid
1H-indole-2,5-dicarboxylic acid
5-phenyl-2,4-pyrrolidinedicarboxylic acid
5-methyl-2,4-pyrrolidinedicarboxylic acid
trans-2,4-azetidinedicarboxylic acid
cis-2,4-azetidinedicarboxylic acid
3,5-piperidinedicarboxylic acid
2,3-pyrrolidinedicarboxylic acid
2,3-azetidinedicarboxylic acid
3,4-pyrrolidinedicarboxylic acid
2,3-dihydro-6H-1,4-dioxino[2,3-c]pyrrole-5,7-dicarboxylic acid
1H-imidazole-2,4-dicarboxylic acid
1-butyl-1H-pyrrole-2,3-dicarboxylic acid
3-amino-1-oxide-2,4-pyridinedicarboxylic acid
2,3-dihydro-5-phenyl-1H-pyrrolizine-6,7-dicarboxylic acid
3a,4,5,9b-tetrahydro-3H-cyclopenta[c]quinoline-4,6-dicarboxylic acid
3a,4,5,9b-tetrahydro-3H-cyclopenta[c]quinoline-4,8-dicarboxylic acid
2,3-dihydro-1H-imidazole-4,5-dicarboxylic acid
5-amino-6-methyllutidinic acid
1H-indole-3,7-dicarboxylic acid
3,3-dimethyl-2,6-piperidinedicarboxylic acid
1-butyl-2,5-pyrrolidinedicarboxylic acid
1H-indole-4,6-dicarboxylic acid
1-(phenylmethyl)-3,4-pyrrolidinedicarboxylic acid
3-(carboxymethyl)-1H-indole-2,6-dicarboxylic acid
3,4-bis(2,2,2-trifluoroethyl)-1H-pyrrole-2,5-dicarboxylic acid
9-hexyl-9H-carbazole-3,6-dicarboxylic acid
3-methyl-5-(1-piperazinylsulfonyl)-2,4-thiophenedicarboxylic acid
2,3,4,9-tetrahydro-1H-carbazole-5,7-dicarboxylic acid
2,3-dimethyl-1H-indole-4,6-dicarboxylic acid
7-amino-1,4-dihydro-4-oxo-3,6-quinolinedicarboxylic acid
5-amino-3-methyl-2,4-thiophenedicarboxylic acid
(m-tolylimino)diacetic acid
(o-tolylimino)diacetic acid
D-cystathionine
phenethyliminodiacetic acid
2-benzyl-2,2'-iminodiacetic acid
L-α-glutamyl-L-alanyl-L-alanine
N,N'-dibenzylethylenediaminediacetic acid
N-L-γ-glutamyl-D-alanine
glycyl-L-glutamylglycine
N-(carboxymethyl)-N-(tetrahydro-1,1-dioxido-3-thienyl)glycine
N-(2-carboxyethyl)-N-phenyl-beta-alanine
N-(carboxymethyl)-N-octylglycine
N-(tert-butoxycarbonyl)iminodiacetic acid
N-(carboxymethyl)-L-alanine N-(6-aminohexyl)-N-(carboxymethyl)glycine
N-(carboxymethyl)-N-tetradecylglycine
N-(1-carboxyethyl)-D-alanine
N-(carboxymethyl)-D-alanine
decyliminodiacetic acid
3,3'-(dimethylhydrazono)bis-propanoic acid
N-(carboxymethyl)-N-[2-(2,6-dioxo-4-morpholinyl)ethyl] glycine
N-alpha-aspartylglycine
N-beta-aspartylglycine
N-L-alpha-aspartyl-beta-alanine
3,4-xylylamino-N,N-diacetic acid
N-(1-carboxyethyl)alanine
N-(carboxymethyl)alanine
N,N'-methylenebis-glycine
N-(aminomethyl)-N-(carboxymethyl)glycine
N-(aminomethyl)-N-(carboxymethyl)glycine
2,2'-(methylhydrazono)bis-acetic acid
N-(2-carboxyethyl)-N-(4-methylphenyl)-beta-alanine
N-(2-carboxyethyl)-N-(3-methylphenyl)-beta-alanine
3-[(carboxymethyl)amino]alanine
D-alpha-aspartyl-D-alanine
N-(2-carboxyethyl)-N-(1-oxohexadecyl)-beta-alanine
N-(2-carboxyethyl)-N-(1-oxodecyl)-beta-alanine
N-(2-carboxyethyl)-N-(1-oxotetradecyl)-beta-alanine
amino[(carboxymethyl)thio]acetic acid
N,N'-1,6-hexanediylbis-beta-alanine
N-(carboxymethyl)-N-phenyl-beta-alanine
N-(1-carboxyethyl)-L-alanine
L-glutamic acid
L-aspartic acid.

Mention may also be made, alone or as a mixture, of the following tricarboxylic and tetracarboxylic acids, and also the anhydrides thereof:
3,3',3''-[1,2,3-propanetriyltris(oxy)]tris-propanoic acid
pyrazinetricarboxylic acid
4-(3-carboxyphenyl)-2,5-pyridinedicarboxylic acid
3-(carboxymethyl)-2,4-quinolinedicarboxylic acid
3-(carboxymethyl)-1H-indole-2,5-dicarboxylic acid
3-C-carboxy-2-deoxy-D-threo-pentaric acid
hydroxycitric acid
D-glucopyranuronosyl-D-arabino-2-hexulofuranosidaric acid
2,3,5,6-pyridinetetracarboxylic acid
N,N'-1,2-ethanediylbis[N-(carboxymethyl)-β-alanine
L-α-aspartyl-L-aspartic acid
4-[bis(carboxymethyl)amino]benzoic acid
7-[bis(carboxymethyl)amino]heptanoic acid
N-(2-carboxyethyl)aspartic acid
3-[bis(2-carboxyethyl)amino]benzoic acid
4-[bis(2-carboxyethyl)amino]benzoic acid.

6,6'-[(1,2-Dioxo-1,2-ethanediyl)diimino]bis-hexanoic acid, 2,2'-sulfinylbis-acetic acid, 4,13-dioxo-3,5,12,14-tetraazahexadecanedioic acid, poly(ethylene glycol)disuccinate, poly(ethylene glycol)bis(carboxymethyl)ether, 8-[(carboxymethyl)amino]-8-oxooctanoic acid, 2,2'-[methylenebis(sulfonyl)]bis-acetic acid, 4,4'-(1,6-hexanediyldiimino)bis[4-oxobutanoic acid], 4,9-dioxo-3,5,8,10-tetraazadodecanedioic acid, 4-[(1-carboxyethyl)amino]-4-oxobutanoic acid, 6-[(3-carboxy-1-oxopropyl)amino]hexanoic acid, N,N'-(1,6-dioxo-1,6-hexanediyl)bis-glycine, N,N'-(1,3-dioxo-1,3-propanediyl)bis-glycine, 4,7,9,12-tetraoxapentadecanedioic acid, 4-pyranone-2,6-dicarboxylic acid, 2,5-pyrazinedicarboxylic acid, 1H-imidazole-4,5-dicarboxylic acid, 2,6-pyrazinedicarboxylic acid, 2,5-furandicarboxylic acid, 3,4-furandicarboxylic acid, 2,3-furandicarboxylic acid, 2,5-diphenyl-3,4-furandicarboxylic acid, 2-methyl-3,4-furandicarboxylic acid, D-tartaric acid, D,L-tartaric acid, L-tartaric acid, galactaric acid, D-glucaric acid; 2,5-pyridinedicarboxylic acid, 2,5-pyrrolidinedicarboxylic acid, 1-phenyl-1H-pyrrole-3,4-dicarboxylic acid, 2,4-pyrrolidinedicarboxylic acid, 5-phenyl-2,4-pyrrolidinedicarboxylic acid, 3,5-piperidinedicarboxylic acid, 3,4-pyrrolidinedicarboxylic acid, 1-butyl-2,5-pyrrolidinedicarboxylic acid, 1-(phenylmethyl)-3,4-pyrrolidinedicarboxylic acid, N-(2-carboxyethyl)-N-phenyl-β-alanine, N-(carboxymethyl)-N-octylglycine, N-(1-carboxyethyl)-L-alanine, L-glutamic acid, L-aspartic acid and N-(2-carboxyethyl)aspartic acid; and mixtures thereof, may preferably be used.

2,2'-Sulfinylbis-acetic acid, 2,2'-[methylenebis(sulfonyl)]bis-acetic acid, N,N'-(1,3-dioxo-1,3-propanediyl)bis-glycine, 2,5-furandicarboxylic acid, D-tartaric acid, D,L-tartaric acid, L-tartaric acid, galactaric acid, L-glutamic acid and L-aspartic acid, and mixtures thereof, will be most particularly preferred.

A lactone comprising at least one carboxylic group, especially 1, 2 or 3 COOH groups, may also be used. Preferably, the lactones contain 5 to 14 carbon atoms and especially 6 to 13 or even 6 to 12 carbon atoms.

Mention may be made most particularly, alone or as a mixture, of the following lactones:
tetrahydro-2,2-dimethyl-5-oxo-3-furancarboxylic acid
4,7,7-trimethyl-3-oxo-2-oxabicyclo[2.2.1]heptane-1-carboxylic acid
4,6-dimethyl-2-oxo-2H-pyran-5-carboxylic acid
2-oxo-2H-pyran-5-carboxylic-2-pentenedioic acid
2-oxo-2H-1-benzopyran-3-carboxylic acid
2-oxo-2H-pyran-6-carboxylic acid
1,3-dihydro-3-oxo-1-isobenzofurancarboxylic acid
4-methyl-2-oxo-2H-1-benzopyran-3-carboxylic acid
1-oxo-1H-2-benzopyran-3-carboxylic acid
8-methoxy-2-oxo-2H-1-benzopyran-3-carboxylic acid
2-oxo-1-oxaspiro[4.5]decane-4-carboxylic acid
2-oxo-2H-pyran-3-carboxylic acid
4-methyl-2-oxo-2H-pyran-6-carboxylic acid
3-oxo-3H-naphtho[2,1-b]pyran-2-carboxylic acid
tetrahydro-5-oxo-2,3-furandicarboxylic acid
1,3-dihydro-3-oxo-4-isobenzofurancarboxylic acid
1,3-dihydro-1-oxo-5-isobenzofurancarboxylic acid
hexahydro-2-oxo-3,5-methano-2H-cyclopenta[b]furan-7-carboxylic acid
6-methyl-2,4-dioxo-2H-pyran-5-carboxylic acid
1-oxo-3-isochromancarboxylic acid
2-oxo-2H-1-benzopyran-6-carboxylic acid
6-methyl-2-oxo-2H-1-benzopyran-3-carboxylic acid
2,5-dihydro-4,5,5-trimethyl-2-oxo-3-furancarboxylic acid
tetrahydro-5-oxo-2-phenyl-3-furancarboxylic acid
tetrahydro-5-oxo-4-propyl-2-furoic acid
2-butyl-2,3-dideoxypentaric acid
2-oxo-2H-1-benzopyran-7-carboxylic acid
2-oxo-1-oxaspiro[4.4]nonane-4-carboxylic acid
4-ethyltetrahydro-5-oxo-2-furoic acid
5-ethyltetrahydro-2,3-dimethyl-6-oxo-2H-pyran-2-carboxylic acid
7-methoxy-2-oxo-2H-1-benzopyran-3-carboxylic acid
2-oxo-2H-1-benzopyran-4-carboxylic acid
2-oxo-6-pentyl-2H-pyran-3-carboxylic acid
7-oxo-4-oxepanecarboxylic acid
3-(carboxymethyl)-2,3-dideoxypentaric acid
2,3-dihydro-2-oxo-7-benzofurancarboxylic acid
1,3,4,5-tetrahydro-1-oxo-2-benzoxepin-7-carboxylic acid
3,4-dihydro-3-oxo-1H-2-benzopyran-6-carboxylic acid
2,3,4,5-tetrahydro-2-oxo-1-benzoxepin-7-carboxylic acid
3,4-dihydro-1-oxo-1H-2-benzopyran-8-carboxylic acid 1,3,4,5-tetrahydro-3-oxo-2-benzoxepin-9-carboxylic acid
1,3,4,5-tetrahydro-3-oxo-2-benzoxepin-7-carboxylic acid
3,4-dihydro-2-oxo-2H-1-benzopyran-8-carboxylic acid
1,3,4,5-tetrahydro-1-oxo-2-benzoxepin-9-carboxylic acid
3,4-dihydro-1-oxo-1H-2-benzopyran-6-carboxylic acid
3,4-dihydro-3-oxo-1H-2-benzopyran-8-carboxylic acid
2,3,4,5-tetrahydro-2-oxo-1-benzoxepin-9-carboxylic acid
isocitric acid lactone
5-oxo-2-tetrahydrofurancarboxylic acid.

Tetrahydro-5-oxo-2,3-furandicarboxylic acid, 1,3-dihydro-3-oxo-4-isobenzofurancarboxylic acid, 1,3-dihydro-1-oxo-5-isobenzofurancarboxylic acid, tetrahydro-5-oxo-2-phenyl-3-furancarboxylic acid, isocitric acid lactone and 5-oxo-2-tetrahydrofurancarboxylic acid, and mixtures thereof, may preferably be used.

The said polycarboxylic acid and/or the cyclic anhydride and/or the lactone thereof, and mixtures thereof, preferably represents 5% to 60% by weight, especially 10% to 40% by weight and better still 12% to 25% by weight, relative to the total weight of the polycondensate forming the polymer backbone.

The polycondensate capable of leading to the polymer backbone must moreover comprise at least one free OH group, capable of reacting chemically with the isocyanate groups borne by the junction group; this especially implies that it has a non-zero hydroxyl number, especially between 5 and 200 and better still between 10 and 150, expressed in mg of potassium hydroxide per g of polycondensate.

The said polymer backbone bearing hydroxyl groups OH may thus be represented schematically in the following manner: POL-(OH)n, with n=integer greater than or equal to 1.

The polymer according to the invention also comprises at least one junction group linked to the said polymer backbone and capable of establishing H bonds with one or more partner junction groups, of identical or different chemical nature, each pairing of a junction group involving at least 3H (hydrogen) bonds, preferably at least 4H bonds and preferentially 4H bonds.

For the purposes of the invention, the term "junction group" means any functional group comprising groups that are donors or acceptors of H bonds, and capable of establishing at least 3H bonds, preferably at least 4H bonds and preferentially 4H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The said junction group preferably bears at least one isocyanate group, capable of reacting with the hydroxyl groups borne by the polymer backbone, so as to form a urethane function, bonding the said backbone to the said junction group. It should be noted that the said urethane function should be considered as forming an integral part of the junction group; it is thus capable of intervening in the formation of 3H bonds by the said junction group.

The said junction group bearing isocyanate groups may be represented schematically in the following manner: OCN-A-NCO or B—NCO, depending on whether it comprises one or two NCO groups.

The divalent radical A may be a saturated or unsaturated, linear or branched, cyclic or non-cyclic, aromatic or non-aromatic aliphatic divalent radical, which contains 1 to 40 carbon atoms, optionally comprising one or more heteroatoms chosen from O, S and/or N, and/or optionally substituted with one or more fluorine atoms and/or hydroxyl radicals, and mixtures thereof.

The radical A may especially be a linear or branched $C_1$-$C_{30}$ alkyl group or a $C_4$-$C_{12}$ cycloalkyl group or a $C_4$-$C_{12}$ aryl group; optionally substituted with an ester and/or amide function.

It may, for example, have the structure —$(CH_2)_c$—, —$(CHR)_c$— or —$(CRR')_c$— in which R and R', which may be identical or different, represent a linear or branched $C_1$-$C_{30}$ alkyl group and c is an integer from 1 to 30 and preferably from 1 to 12;
or alternatively of structure:

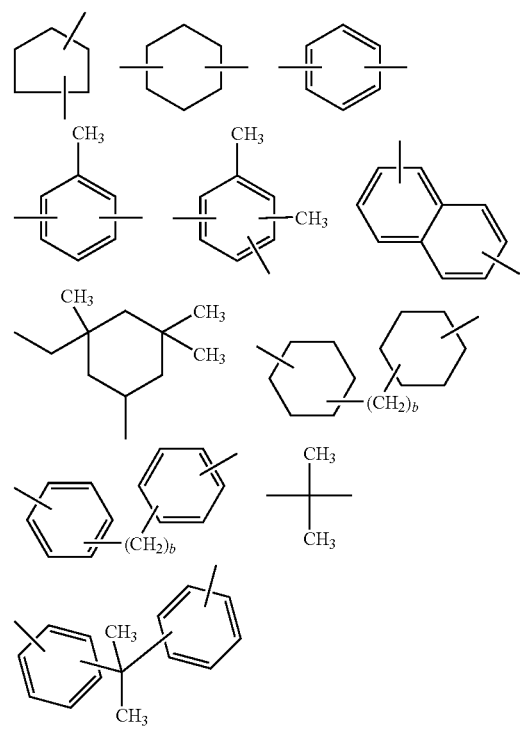

in which b is an integer between 0 and 3;
and also any combination of these structures.

Among the divalent radicals A that are particularly preferred, mention may be made of the radicals 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene); 4,4'-methylenebis(cyclohexyl-1,4-cyclohexylene); 2,4-tolylene, 2,6-tolylene; 1,5-naphthylene; 4,4'-methylenebis(phenyl); tetramethylxylylene; and the divalent radical derived from isophorone, of structure:

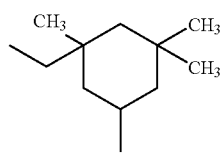

Thus, the junction groups OCN-A-NCO that are particularly preferred may be chosen from the following compounds:

1,4-diisocyanatobutane; 1,6-hexamethylene diisocyanate or 1,6-diisocyanatohexane; 1,5-diisocyanato-2-methylpentane; 1,4-diisocyanato-4-methylpentane; 1,6-diisocyanato-2, 2,4-trimethylhexane; 1,6-diisocyanato-2,4,4-trimethylhexane; 1,5-diisocyanato-5-methylhexane; 3(4)-isocyanatomethyl-1-methylcyclohexyl isocyanate; 1,6-diisocyanato-6-methylheptane; 1,5-diisocyanato-2,2,5-trimethylhexane; 1,7-diisocyanato-3,7-dimethyloctane; 1-isocyanato-1,2,2-trimethyl-3-(2-isocyanatoethyl)cyclopentane; 1-isocyanato-n-butyl-3-(4-isocyanatobut-1-yl)cyclopentane; 1-isocyanato-1,2-dimethyl-3-ethyl-3-isocyanatomethylcyclopentane; 1-isocyanato-1-methyl-4-(4-isocyanatobut-2-yl)cyclohexane; 1-isocyanato-1,4-dimethyl-4-isocyanatomethylcyclohexane; 1-isocyanato-1, 3-dimethyl-3-isocyanatomethylcyclohexane; 1,3-bis (isocyanatomethyl)cyclohexane; isophorone diisocyanate; 4,4'-methylenebis(cyclohexyl isocyanate); 1,4-diphenylene diisocyanate; tolylene 2,4-diisocyanate; tolylene 2,6-diisocyanate; 1,3-bis(isocyanatomethyl)benzene; 4,4'-methylenebis (phenyl isocyanate); naphthalene diisocyanate; tetramethyl-1,3-xylylenediisocyanate.

These diisocyanates may obviously be used alone or in the form of a mixture of two or more diisocyanates.

The divalent radical A may also have the structure:

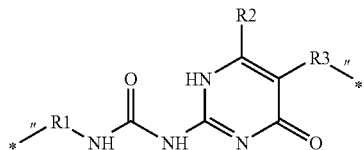

in which:

R1 and R3, which may be identical or different, represent a divalent carbon-based radical chosen from (i) a linear or branched $C_1$-$C_{30}$ alkyl group, (ii) a $C_4$-$C_{12}$ cycloalkyl group and (iii) a $C_4$-$C_{12}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents H, halogen (Br, Cl or F) or a linear, branched or cyclic, saturated or unsaturated, optionally aromatic $C_1$-$C_{32}$ monovalent hydrocarbon-based group, which may contain one or more heteroatoms chosen from O, S, N, P and F.

The radical R2 may especially be H, or alternatively:
a $C_1$-$C_{32}$ alkyl group;
a $C_4$-$C_{12}$ cycloalkyl group;
a $C_4$-$C_{12}$ aryl group
a ($C_4$-$C_{12}$)aryl($C_1$-$C_{18}$)alkyl group;
a $C_1$-$C_4$ alkoxy group;
an arylalkoxy group, in particular a ($C_1$-$C_4$)arylalkoxy group;
a $C_4$-$C_{12}$ heterocycle;
or a combination of these radicals, which may be optionally substituted with an amino, ester and/or hydroxyl function.

Preferably, R2 represents H, $CH_3$, $C_{13}H_{27}$, $C_7H_{15}$, phenyl, isopropyl, isobutyl, n-butyl, tert-butyl or propyl.

More preferably, the divalent radical A may have the formula:

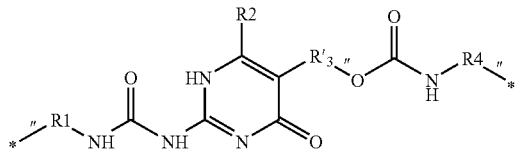

in which R1 and R2 are as above, and R'3 and R4, which may be identical or different, represent a divalent carbon-based radical chosen from a linear or branched $C_1$-$C_{30}$ alkyl group or a $C_4$-$C_{12}$ cycloalkyl group or a $C_4$-$C_{12}$ aryl group; or a mixture thereof.

Even more preferentially, the radical A may have the formula:

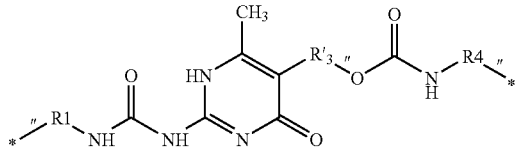

in which R1, R'3 and R4 are as defined above.

Preferentially, the radicals R1, R3, R'3 and R4, independently of each other, may be chosen from the following radicals: methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1, 3-phenylene; 4,4'-biphenylenemethylene, 1,2-tolylene, 1,4-tolylene, 2,4-tolylene, 2,6-tolylene; 1,5-naphthylene; 4,4'-methylenebis(phenyl); tetramethylxylylene; the divalent radical derived from isophorone.

In a particularly preferred manner, R1, R3, R'3 and R4 represent, independently of each other, —$(CH_2)_2$—, —$(CH_2)_6$—, —$CH_2CH(CH_3)CH_2C(CH_3)_2CH_2CH_2$—, or an -isophorone-radical; and better still R1=R4=-isophorone- and R'3=—$(CH_2)_2$—, which leads to the following very preferred radical:

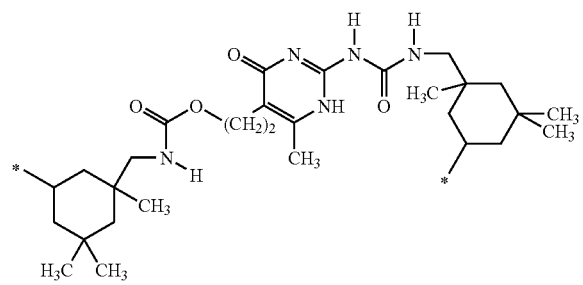

Thus, the junction groups OCN-A-NCO that are particularly preferred may also be chosen from the compounds of formula:

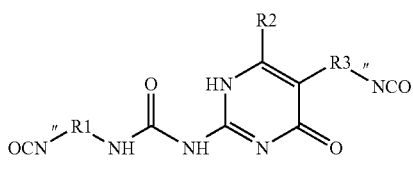

in which R1, R2 and R3 are as defined above, and preferably from the compounds of formula:

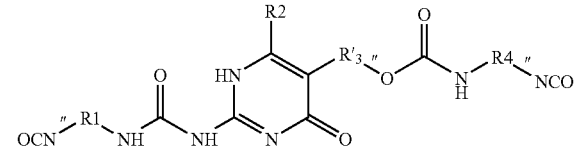

in which R'3 and R4, which may be identical or different, represent a divalent carbon-based radical chosen from a linear or branched $C_1$-$C_{30}$ alkyl group, a $C_4$-$C_{12}$ cycloalkyl group or a $C_4$-$C_{12}$ aryl group; or mixtures thereof.

Even more preferentially, the junction group may be of formula:

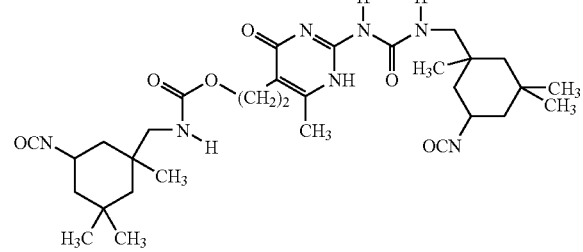

The monovalent radical B may be of formula:

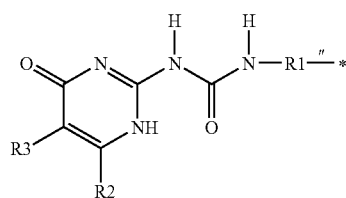

in which:

the radical R1 represents a divalent carbon-based group chosen from (i) a linear or branched $C_1$-$C_{30}$ alkyl group, (ii) a $C_4$-$C_{12}$ cycloalkyl group and (iii) a $C_4$-$C_{12}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

the radicals R2 and R3, which may be identical or different, represent a hydrogen atom or a linear, branched or cyclic, saturated or unsaturated $C_1$-$C_{32}$ carbon-based, especially hydrocarbon-based (alkyl), radical, which may comprise one or more heteroatoms chosen from O, N, S, F, Si and P.

Preferably, R1 represents a $C_2$-$C_{10}$ alkyl group and may be chosen from 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene); -isophorone-, 4,4'-methylenebiscyclohexylene, tolylene, 2-methyl-1,3-phenylene, 4-methyl-1,3-phenylene and 4,4-bisphenylenemethylene.

Preferentially, R1 represents -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4-methylenebiscyclohexylene or 2-methyl-1,3-phenylene.

Preferably, R2 represents a $C_1$-$C_{16}$ or even $C_1$-$C_{10}$ alkyl radical and especially methyl, ethyl, isopropyl, propyl, isobutyl, n-butyl, tert-butyl or —CH(C$_2$H$_5$)(C$_4$H$_9$).

Preferably, R3 represents H.

Preferentially, the following may be possible:

R1=-isophorone-, R2=methyl and R3=H, which leads to the radical:

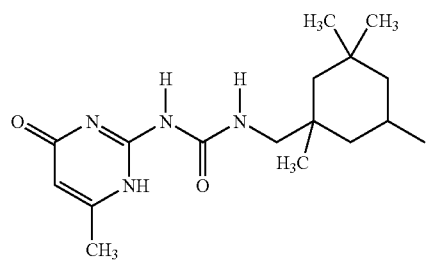

R1=-(CH$_2$)$_6$—, R2=methyl and R3=H, which leads to the radical:

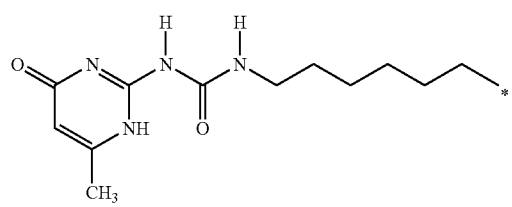 [SMILES: CCCCCCCNC(=O)Nc1nc(=O)cc(C)[nH]1]

R1=-(CH$_2$)$_6$—, R2=isopropyl and R3=H, which leads to the radical:

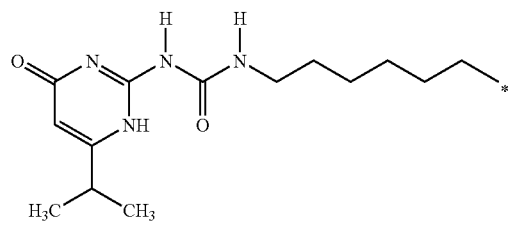 [SMILES: CCCCCCCNC(=O)Nc1nc(=O)cc(C(C)C)[nH]1]

The junction group B—NCO may thus be chosen from the compounds of formula:

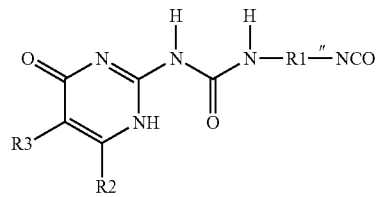

in which R1, R2 and R3 are as defined above; and may be chosen especially from the following groups:

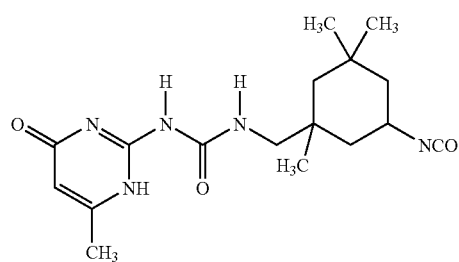

-continued

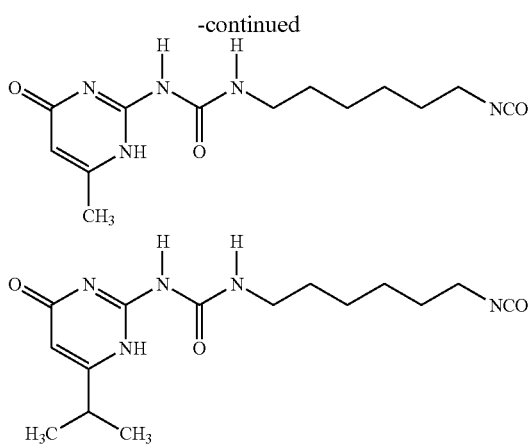

Preferably, the polymer according to the invention has a viscosity, measured at 125° C., of between 30 and 5000 mPa·s, especially between 150 and 3500 mPa·s, or even between 500 and 3000 mPa·s and better still between 750 and 2500 mPa·s. This viscosity is measured in the manner described before the examples.

Moreover, the polymer according to the invention is advantageously soluble in the commonly employed cosmetic oily media, and especially in plant oils, alkanes, fatty esters, short esters, fatty alcohols and silicone oils, and more particularly in media comprising isododecane, Parleam, isononyl isononanoate, octyldodecanol, phenyl trimethicone, a $C_{12}$-$C_{15}$ alkyl benzoate, butyl acetate, ethyl acetate and/or D5 (decamethylcyclopentasiloxane).

The term "soluble" means that the polymer forms a clear solution in at least one solvent chosen from isododecane, Parleam, isononyl isononanoate, octyldodecanol, phenyl trimethicone, a $C_{12}$-$C_{15}$ alkyl benzoate, butyl acetate, ethyl acetate and D5 (decamethylcyclopentasiloxane), in a proportion of at least 50% by weight, at 25° C.

The number-average molecular mass Mn of the polymer before functionalization according to the invention is preferably between 1000 and 3 000 000, preferably between 5000 and 1 000 000 and better still between 8000 and 500 000. The molecular weight of the final polymer obviously varies as a function of the degree of functionalization (i.e. degree of grafting of the free OHs of the polycondensate).

Preferably, the degree of grafting of the free OHs of the polycondensate is between 1% and 80%, especially between 2% and 50% and better still between 5% and 25%; however, this degree may also be 100% (all of the free OHs are functionalized with a junction group).

The functionalized polymer according to the invention may result from one of the following chemical reactions:

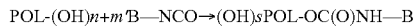

with m, m' and n being greater than or equal to 1, preferably with m≤n/2 and m'<n; r, r' and s preferably being non-zero.

The polymer forming the polymer backbone according to the invention may be prepared via the esterification/polycondensation processes usually employed by a person skilled in the art. By way of illustration, a general preparation process consists in:

mixing the polyol and the aromatic and non-aromatic monocarboxylic acids, heating the mixture under an inert atmosphere, first to the melting point (generally 100-130° C.) and then to a temperature of between 150 and 220° C. until the monocarboxylic acids have been totally consumed (reached when the acid number is less than or equal to 1) preferably while distilling off the water gradually as it is formed, and then optionally cooling the mixture to a temperature of between 90 and 150° C., adding the polycarboxylic acid and/or the cyclic anhydride and/or the lactone, in a single portion or sequentially, and then heating again to a temperature of less than or equal to 220° C., especially between 170 and 220° C., preferably while continuing to remove the water formed, until required characteristics in terms of acid number, viscosity, hydroxyl number and solubility are obtained.

Thus, in a first stage, the polycondensate that will form the polymer backbone is obtained.

It is possible to add conventional esterification catalysts, for example of sulfonic acid type (especially to a weight concentration of between 1% and 10%) or of titanate type (especially to a weight concentration of between 5 and 100 ppm). It is also possible to perform the reaction, totally or partly, in an inert solvent such as xylene and/or under reduced pressure, to facilitate the removal of the water. Advantageously, neither catalyst nor solvent is used.

The said preparation process may also comprise a step of adding at least one antioxidant to the reaction medium, especially to a weight concentration of between 0.01% and 1% relative to the total weight of monomers, so as to limit any degradation associated with prolonged heating. The antioxidant may be of primary type or secondary type, and may be chosen from hindered phenols, aromatic secondary amines, organophosphorus compounds, sulfur compounds, lactones and acrylic bisphenols; and mixtures thereof.

The final polymer may be obtained by formation of a urethane bond, between the free hydroxyl functions of the polycondensate described above and the isocyanate functions borne by the junction group. By way of illustration, a general preparation process consists in:

heating the polycondensate obtained above, comprising at least one hydroxyl function, to a temperature that is high enough to be able to stir the polymer without addition of a solvent. Typically, this temperature may be between 80° C. and 140° C.;

adding the junction group bearing the isocyanate functions;

stirring this mixture vigorously, under a controlled atmosphere, at a temperature of about 130° C.;

monitoring by infrared spectroscopy the characteristic band for isocyanates (between 2500 and 2800 cm$^{-1}$) so as to stop the reaction on total disappearance of the peak, and then allowing the final product to return to room temperature.

A solvent may be used if the viscosity of the initial polycondensate is too high, even after heating to 80-140° C., preventing stirring of this polycondensate. It is also possible to add a conventional catalyst for the formation of a urethane bond, when the reaction takes place too laboriously. An example that may be mentioned is dibutyltin dilaurate.

The use of the polymers according to the invention in a cosmetic composition leads, after applying this composition to keratin materials, to the formation of a supramolecular polymer.

For the purposes of the invention, the term "supramolecular polymer" means a polymer chain or network formed from the assembly of a polymer according to the invention with at least one other polymer according to the invention, which may be identical or different, each assembly comprising at least one pair of paired junction groups, which may be identical or different.

For the purposes of the invention, the term "pair of paired junction groups" means two junction groups, each of which may or may not be borne by the same polymer according to the invention, the two groups being connected together via at least three H bonds, preferably at least 4H bonds and more preferentially 4 H bonds.

Thus, the supramolecular polymer will have physical crosslinking points provided by the H bonds between these pairs of junction groups. The physical crosslinking will ensure the maintenance and persistence of the cosmetic effect in a similar manner to chemical crosslinking, while at the same time allowing reversibility, i.e. the possibility of totally removing the deposit.

It has been found that the use of the polymers according to the invention may lead, after applying the composition to keratin materials, either to the formation of a supramolecular polymer in the form of a physically crosslinked three-dimensional network, which is generally in the form of a film, with very good mechanical strength, or to the formation of a supramolecular polymer in the form of a long polymer chain, generally of high molecular mass, resulting from the physical connection of the polymers of the invention.

The polymers according to the invention may be used very advantageously in a cosmetic composition that moreover comprises a cosmetically acceptable medium, i.e. a medium that is compatible with skin tissue such as facial or bodily skin, and keratin materials such as the hair, the eyelashes, the eyebrows and the nails.

The amount of polymer present in the compositions obviously depends on the type of composition and on the desired properties, and may vary within a very wide range, generally of between 0.1% and 80% by weight, preferably between 1% and 50% by weight, especially between 10% and 45% by weight, or even between 20% and 40% by weight and better still between 25% and 35% by weight relative to the weight of the final cosmetic composition.

The composition may then comprise, according to the intended application, constituents that are common for this type of composition.

The composition according to the invention may advantageously comprise a liquid fatty phase, which may constitute a solvent medium for the polymers according to the invention, and which may comprise at least one compound chosen from volatile or non-volatile carbon-based, hydrocarbon-based, fluoro and/or silicone oils and/or solvents of mineral, animal, plant or synthetic origin, alone or as a mixture, provided that they form a uniform, stable mixture and are compatible with the intended use.

For the purposes of the invention, the term "volatile" means any compound that is capable of evaporating on contact with keratin materials, or the lips, in less than one hour at room temperature (25° C.) and atmospheric pressure (1 atm). In particular, this volatile compound has a non-zero vapour pressure, at room temperature and atmospheric pressure, especially ranging from 0.13 Pa to 40 000 Pa ($10^3$ to 300 mm Hg), in particular ranging from 1.3 Pa to 13 000 Pa (0.01 to 100 mm Hg) and more particularly ranging from 1.3 Pa to 1300 Pa (0.01 to 10 mm Hg).

In contrast, the term "non-volatile" refers to a compound that remains on keratin materials or the lips at room temperature and atmospheric pressure for at least one hour, and which especially has a vapour pressure of less than $10^{-3}$ mm Hg (0.13 Pa).

Preferably, the physiologically acceptable medium of the composition according to the invention may comprise, in a liquid fatty phase, at least one oil and/or solvent that may be chosen, alone or as a mixture, from:

1/ Esters of monocarboxylic acids with monoalcohols and polyalcohols; advantageously, the said ester is a $C_{12}$-$C_{15}$ alkyl benzoate or corresponds to the following formula: R'1-COO—R'2 in which: R'1 represents a linear or branched alkyl radical of 1 to 40 carbon atoms and preferably of 7 to 19 carbon atoms, optionally comprising one or more ethylenic double bonds, optionally substituted, and the hydrocarbon-based chain of which may be interrupted with one or more heteroatoms chosen from N and O and/or one or more carbonyl functions, and R'2 represents a linear or branched alkyl radical of 1 to 40 carbon atoms, preferably 3 to 30 carbon atoms and better still 3 to 20 carbon atoms, optionally comprising one or more optionally substituted ethylenic double bonds, and the hydrocarbon-based chain of which may be interrupted with one or more heteroatoms chosen from N and O and/or one or more carbonyl functions.

The term "optionally substituted" means that R'1 and/or R'2 may bear one or more substituents chosen, for example, from groups comprising one or more heteroatoms chosen from O and/or N, such as amino, amine, alkoxy and hydroxyl.

Examples of groups R'1 are those derived from fatty acids, preferably higher fatty acids, chosen from the group formed by acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, oleostearic acid, arachidonic acid and erucic acid, and mixtures thereof.

Preferably, R'1 is a branched, unsubstituted alkyl group of 4 to 14 carbon atoms and preferably of 8 to 10 carbon atoms, and R'2 is a branched, unsubstituted alkyl group of 5 to 15 carbon atoms and preferably of 9 to 11 carbon atoms.

Mention may be made in particular, preferably, of $C_8$-$C_{48}$ esters, optionally incorporating in their hydrocarbon-based chain one or more heteroatoms chosen from N and O and/or one or more carbonyl functions; and more particularly purcellin oil (cetostearyl octanoate), isononyl isononanoate, isopropyl myristate, isopropyl palmitate, 2-ethylhexyl palmitate, 2-octyldodecyl stearate, 2-octyldodecyl erucate, isostearyl isostearate, a $C_{12}$ to $C_{15}$ alkyl benzoate, hexyl laurate or diisopropyl adipate; and heptanoates, octanoates, decanoates or ricinoleates of alcohols or of polyalcohols, for example of fatty alcohols, for instance propylene glycol dioctanoate, and also isopropyl N-lauroyl sarcosinate (especially Eldew-205SL from Ajinomoto); hydroxylated esters, for instance isostearyl lactate or diisostearyl malate; and pentaerythritol esters; branched $C_8$-$C_{16}$ esters, especially isohexyl neopentanoate.

2/ Hydrocarbon-based plant oils with a high triglyceride content, formed from fatty acid esters of glycerol in which the fatty acids may have varied chain lengths from $C_4$ to $C_{24}$, these chains possibly being linear or branched, and saturated or unsaturated; these oils are especially wheatgerm oil, corn oil, sunflower oil, shea oil, castor oil, sweet almond oil, macadamia oil, apricot oil, soyabean oil, rapeseed oil, cotton seed oil, alfalfa oil, poppy seed oil, pumpkin oil, sesame seed oil, marrow oil, avocado oil, hazelnut oil, grapeseed oil, blackcurrent seed oil, evening primrose oil, millet oil, barley oil, quinoa oil, olive oil, rye oil, safflower oil, candlenut oil, passionflower oil, musk rose oil, jojoba oil, palm oil or beauty-leaf oil; or alternatively caprylic/capric acid triglycerides, for instance those sold by the company Stearinerie Dubois or those sold under the names Miglyol 810®, 812® and 818® by the company Dynamit Nobel.

3/ Alcohols, and especially $C_6$-$C_{32}$ and especially $C_{12}$-$C_{26}$ monoalcohols, for instance oleyl alcohol, linoleyl alcohol, linolenyl alcohol, isostearyl alcohol, 2-hexyldecanol, 2-butyloctanol, 2-undecylpentadecanol and octyldodecanol.

4/ Linear or branched, volatile or non-volatile hydrocarbon-based oils, of synthetic or mineral origin, which may be chosen from hydrocarbon-based oils containing from 5 to 100 carbon atoms, and especially petroleum jelly, polydecenes, hydrogenated polyisobutenes such as Parleam, squalane and perhydrosqualene, and mixtures thereof.

Mention may be made more particularly of linear, branched and/or cyclic $C_5$-$C_{48}$ alkanes, and preferentially branched $C_8$-$C_{16}$ alkanes, for instance $C_8$-$C_{16}$ isoalkanes of petroleum origin (also known as isoparaffins); especially decane, heptane, dodecane and cyclohexane; and also isododecane, isodecane and isohexadecane.

5/ Volatile or non-volatile silicone oils. Volatile silicone oils that may be mentioned include linear or cyclic volatile silicone oils, especially those with a viscosity of less than 8 centistokes, and especially containing from 2 to 10 silicon atoms, these silicones optionally comprising alkyl or alkoxy groups containing from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and methylhexyldimethylsiloxane, and mixtures thereof.

The non-volatile silicone oils that may be used according to the invention may be polydimethylsiloxanes (PDMS), polydimethylsiloxanes comprising alkyl or alkoxy groups, which are pendant and/or at the end of a silicone chain, each group containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Preferentially, the physiologically acceptable medium of the composition according to the invention comprises, in a liquid fatty phase, at least one oil and/or one solvent chosen, alone or as a mixture, from isododecane, Parleam, isononyl isononanoate, octyldodecanol, phenyl trimethicone, $C_{12}$-$C_{15}$ alkyl benzoates, butyl and ethyl acetates, and/or D5 (decamethylcyclopentasiloxane).

The liquid fatty phase may also comprise additional oils and/or solvents, which may be chosen, alone or as a mixture, from:

fluoro oils such as perfluoropolyethers, perfluoroalkanes, for instance perfluorodecalin, perfluorodamantanes, perfluoroalkyl phosphate monoesters, diesters and triesters and fluoro ester oils;

oils of animal origin;

$C_6$ to $C_{40}$ and especially $C_{10}$-$C_{40}$ ethers; propylene glycol ethers that are liquid at room temperature, such as propylene glycol monomethyl ether, propylene glycol monomethyl ether acetate or dipropylene glycol mono-n-butyl ether;

$C_8$-$C_{32}$ fatty acids, for instance oleic acid, linoleic acid or linolenic acid, and mixtures thereof;

difunctional oils, comprising two functions chosen from ester and/or amide and containing from 6 to 30 carbon atoms, especially 8 to 28 carbon atoms and better still from 10 to 24 carbon atoms, and 4 heteroatoms chosen from O and N; preferably, the amide and ester functions being in the chain;

ketones that are liquid at room temperature (25° C.) such as methyl ethyl ketone, methyl isobutyl ketone, diisobutyl ketone, isophorone, cyclohexanone and acetone;

aldehydes that are liquid at room temperature, such as benzaldehyde and acetaldehyde.

The liquid fatty phase may represent 1% to 90% by weight, especially from 5% to 75% by weight, in particular from 10% to 60% by weight or even from 25% to 55% by weight relative to the total weight of the composition.

The composition according to the invention may advantageously comprise a thickener, which may be chosen in particular from:

silicas, especially hydrophobic silicas, such as those described in document EP-A-898 960 and, for example, sold under the references Aerosil R812® by the company Degussa, Cab-O-Sil TS-530®, Cab-O-Sil TS-610®, Cab-O-Sil TS-720® by the company Cabot, Aerosil R972®, Aerosil R974® by the company Degussa;

clays such as montmorillonite, modified clays such as bentones, for example, stearalkonium hectorite and stearalkonium bentonite, polysaccharide alkyl ethers (especially in which the alkyl group contains from 1 to 24 carbon atoms, preferably from 1 to 10, better still from 1 to 6 and more especially from 1 to 3 carbon atoms) such as those described in document EP-A-898 958.

The amount of thickener in the composition according to the invention may range from 0.05% to 40% by weight, preferably from 0.5% to 20% and better still from 1% to 15% by weight relative to the total weight of the composition.

The composition according to the invention may also comprise at least one wax of plant, animal, mineral or synthetic origin, or even silicone origin.

Mention may be made in particular, alone or as a mixture, of hydrocarbon-based waxes such as beeswax; carnauba wax, candelilla wax, ouricury wax, Japan wax, cork fibre wax or sugar cane wax; paraffin wax or lignite wax; microcrystalline waxes; lanolin wax; montan wax; ozokerites; polyethylene waxes; the waxes obtained by Fischer-Tropsch synthesis; hydrogenated oils, fatty esters and glycerides that are solid at 25° C. Silicone waxes may also be used, among which, mention may be made of alkyl, alkoxy and/or esters of polymethylsiloxane.

The amount of wax in the composition according to the invention may range from 0.1% to 70% by weight, preferably from 1% to 40% by weight and better still from 5% to 30% by weight relative to the total weight of the composition.

The composition according to the invention may also comprise one or more dyestuffs chosen from pulverulent compounds, for instance pigments, fillers, nacres and glitter flakes, and/or liposoluble or water-soluble dyes.

The dyestuffs, especially pulverulent dyestuffs, may be present in the composition in a content of from 0.01% to 50% by weight, preferably from 0.1% to 40% by weight or even from 1% to 30% by weight relative to the weight of the composition.

The term "pigments" should be understood as meaning white or coloured, mineral or organic particles of any shape, which are insoluble in the physiological medium, and which are intended to colour the composition.

The term "nacres" should be understood as meaning iridescent particles of any shape, especially produced by certain molluscs in their shell, or alternatively synthesized.

The pigments may be white or coloured, mineral and/or organic, and interference or non-interference. Among the mineral pigments, mention may be made of titanium dioxide, optionally surface-treated, zirconium oxide or cerium oxide, and also iron oxide, chromium oxide, manganese violet, ultramarine blue, chromium hydrate and ferric blue. Among the organic pigments that may be mentioned are carbon black, pigments of D & C type, and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica with iron oxides, titanium mica especially with ferric blue or with chromium oxide, titanium mica with an organic pigment of the abovementioned type, and also nacreous pigments based on bismuth oxychloride.

The fillers may be mineral or organic, and lamellar or spherical. Mention may be made of talc, mica, silica, kaolin, nylon powder, polyethylene powder, poly-β-alanine powder, polyethylene powder, Teflon, lauroyllysine, starch, boron nitride, tetrafluoroethylene polymer powders, hollow microspheres such as Expancel (Nobel Industrie), Polytrap (Dow Corning) and silicone resin microbeads (for example Tospearls from Toshiba), precipitated calcium carbonate, magnesium carbonate, magnesium hydrogen carbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for instance zinc, magnesium or lithium stearates, zinc laurate or magnesium myristate.

The liposoluble dyes are, for example, Sudan red, DC Red 17, DC Green 6, β-carotene, soyabean oil, Sudan brown, DC Yellow 11, DC Violet 2, DC Orange 5 and quinoline yellow. They may represent 0.01% to 20% and better still from 0.1% to 6% of the weight of the composition.

The water-soluble dyes are, for example, beetroot juice or methylene blue, and may represent from 0.01% to 6% of the total weight of the composition.

The composition may also comprise other ingredients commonly used in cosmetic compositions. Such ingredients may be chosen from antioxidants, fragrances, essential oils, preserving agents, cosmetic active agents, moisturizers, vitamins, ceramides, sunscreens, surfactants, gelling agents, spreading agents, wetting agents, dispersants, antifoams, neutralizers, stabilizers, polymers and especially liposoluble film-forming polymers, and mixtures thereof.

Needless to say, a person skilled in the art will take care to select this or these optional additional compound(s), and/or the amount thereof, such that the advantageous properties of the composition for the use according to the invention are not, or are not substantially, adversely affected by the envisaged addition.

The compositions according to the invention may be in any acceptable form that is common for a cosmetic composition. They may thus be in the form of a suspension, a dispersion, especially of oil in water by means of vesicles; an optionally thickened or even gelled organic or oily solution; an oil-in-water, water-in-oil or multiple emulsion; a gel or a mousse; an oily or emulsified gel; a dispersion of vesicles, especially lipid vesicles; a two-phase or multi-phase lotion; a spray; a lotion, a cream, a pomade, a soft paste, an ointment, a solid cast or moulded especially in stick or dish form, or alternatively a compacted solid.

A person skilled in the art may select the appropriate galenical form, and also the method for preparing it, on the basis of his general knowledge, taking into account firstly the nature of the constituents used, especially their solubility in the support, and secondly the intended application of the composition.

Since the compositions in accordance with the invention have gloss and staying power of the said gloss that are improved relative to the prior art, they may be used for caring for or making up keratin materials such as the hair, the skin, the eyelashes, the eyebrows, the nails, the lips, the scalp, and more particularly for making up the lips, the eyelashes and/or the face.

They may thus be in the form of a product for caring for and/or making up bodily or facial skin, the lips, the eyelashes, the eyebrows, the hair, the scalp or the nails; an antisun or self-tanning product; a haircare product, especially for dying, conditioning and/or caring for the hair; they may advantageously be in the form of a makeup composition, especially a mascara, an eyeliner, a lipstick, a lip gloss, a makeup rouge, an eyeshadow, a foundation, a nail varnish or a nailcare product.

A subject of the invention is also a cosmetic process for treating keratin materials, especially bodily or facial skin, the lips, the nails, the hair and/or the eyelashes, comprising the application to the said materials of a cosmetic composition as defined previously.

This process according to the invention makes it possible especially to care for or make up the said keratin materials, in particular the lips and/or the nails, by applying a composition, especially a lipstick or a lip gloss or a nail varnish according to the invention.

The invention is illustrated in greater detail in the examples that follow.

Method for Measuring the Viscosity

The viscosity at 125° C. of the polymer is measured using a cone-plate viscometer of Brookfield CAP 1000+ type.

The appropriate cone-plate is determined by a person skilled in the art, on the basis of his knowledge, especially:

between 50 and 500 mPa·s, a cone 02 may be used
between 500 and 1000 mPa·s: cone 03 or 05 (for the high values)
between 1000 and 4000 mPa·s: cone 05
between 4000 and 10 000 mPa·s: cone 06

Preferably, the same cone is used as far as is possible when it is desired to compare two polymers.

EXAMPLE 1

A/ Synthesis of Pentaerythrityl Benzoate/Isophthalate/Isostearate 20 g of benzoic acid, 280 g of isostearic acid and 100 g of pentaerythritol are placed in a reactor equipped with a mechanical stirrer, an argon inlet and a distillation system, and the mixture is then gradually heated, under a gentle stream of argon, to 110-130° C. to obtain a uniform solution. The temperature is then increased gradually to 180° C. and maintained for about 2 hours. The temperature is again increased to 220° C. and maintained until an acid number of less than or equal to 1 is obtained, which takes about 11 hours. The mixture is cooled to a temperature of between 100 and 130° C., followed by introduction of 100 g of isophthalic acid, and is again heated gradually to 220° C. for about 11 hours.

405 g of pentaerythrityl benzoate/isophthalate/isostearate polycondensate are thus obtained in the form of a very thick oil.

The polycondensate has a hydroxyl number of 72.

B/ Synthesis of the Polymer Functionalized with Ureidopyrimidones 100 g of the polycondensate prepared above are heated to 110° C., followed by addition of 3.22 g (10 mmol) of isocyanate-monofunctionalized ureidopyrimidone dendrons of structure:

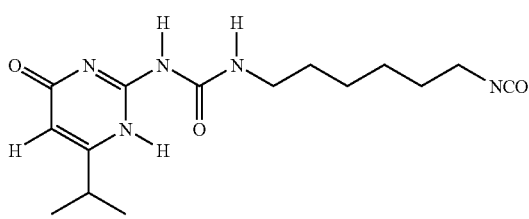

The mixture is stirred and heated under argon at 130° C. for 15 minutes. The reaction is stopped when the peak corresponding to the isocyanate (2250 cm$^{-1}$) in infrared spectroscopy has disappeared.

The final polymer is obtained in the form of a viscous oil. The yield is quantitative. The final polymer has a hydroxyl number of 59, which corresponds to a degree of functionalization of 20%.

C/ Measurement of the Gloss and the Viscosity

The gloss of the above polymer is measured, after spreading a 25 μm film onto black bioskin, after 10 minutes on a plate at 35° C., with a Micro-Trigloss glossmeter. The polymer is conveyed in isododecane at a solids content that makes it possible to obtain, after evaporation of the solvent, a 25 micron film.

The following results are obtained:

|  | Viscosity (125° C.) | Gloss Angle 20°, 60° and 85° |
| --- | --- | --- |
| Polymer according to the invention (obtained in step B) | 1800 mPa · s Cone 5 | 73, 84, 81 |
| Polycondensate obtained in step A | 700 mPa · s Cone 5 | 73, 84, 84 |

It is found that the functionalization with ureidopyrimidones leads to a polymer of higher viscosity, and thus of better staying power, while at the same time maintaining the gloss of the film. Furthermore, the polymer according to the invention conserves its solubility in the commonly used cosmetic oils (especially isododecane).

EXAMPLE 2

49.2 g of the polycondensate prepared in step A of Example 1 above are heated to 100° C., followed by addition of 4.05 g of isocyanate-monofunctionalized ureidopyrimidone dendrons of structure:

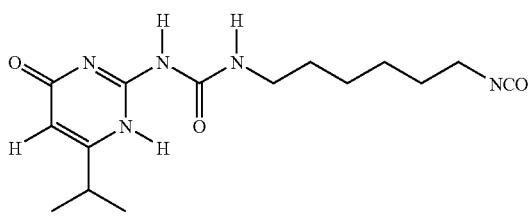

The mixture is stirred and heated under argon at 130° C. for 30 minutes.

The final polymer is obtained in the form of a solid oil. The polymer conveyed in a cosmetic oil (isododecane) makes it possible to obtain a film, after application of the solution and evaporation of the solvent. The gloss of the film is equivalent to that of the polyester before functionalization.

EXAMPLE 3

43.7 g of the polycondensate prepared in step A of Example 1 above are heated to 100° C., followed by addition of 5.35 g of isocyanate-monofunctionalized ureidopyrimidone dendrons of structure:

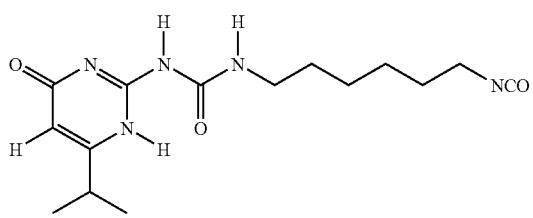

The mixture is stirred and heated under argon at 130° C. for 30 minutes.

The final polymer is obtained in the form of a solid oil. The polymer conveyed in a cosmetic oil (isododecane) makes it possible to obtain a film, after application of the solution and evaporation of the solvent. The gloss of the film is equivalent to that of the polyester before functionalization.

EXAMPLE 4

A/

720 g of benzoic acid, 1392 g of castor oil fatty acids (Nouracid DE 655 from Akzo Nobel) and 916.8 g of pentaerythritol are placed in a 2-liter reactor. The reactor is maintained under an argon atmosphere throughout the synthesis (sparging). The mixture is heated to 130° C. to obtain a uniform solution, and is then maintained at 180° C. for 1 hour. The temperature is increased to 230° C. up to an acid number of less than or equal to 1.

The temperature is reduced to 160° C., and 969.6 g of phthalic anhydride are added, followed by heating at 230° C. After 4 hours, the polymerization kinetics are monitored by means of the acid number. When an acid number of less than 25 is obtained, the synthesis is stopped.

A polymer having an acid number of 23.1 and a hydroxyl number of 165 is obtained.

B/

29.6 g of the polyester synthesized above are dissolved in 50 ml of chloroform in the presence of the catalyst dibutyltin dilaurate. 1.16 g of ureidopyrimidone represented below are added to the reaction medium:

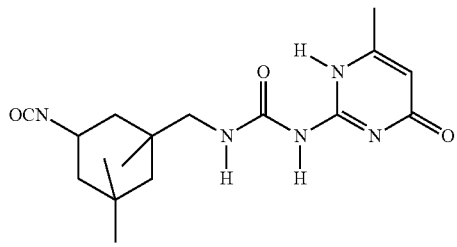

The mixture is stirred under argon at 60° C. for 16 hours. The reaction mixture is then precipitated from 300 ml of hexane, and the precipitate thus obtained is dried under vacuum to give the desired product in the form of a yellow solid.

This yellow solid is soluble at 25° C., to 50% by weight, in solvents such as butyl acetate, and makes it possible to obtain a solution of polymer in a cosmetic solvent.

EXAMPLE 5

29 g of the polyester synthesized in step A of Example 4 are dissolved in 60 ml of chloroform in the presence of the catalyst dibutyltin dilaurate. 2.91 g of the ureidopyrimidone represented below are added to the reaction medium:

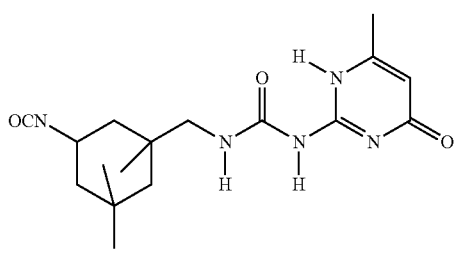

The mixture is stirred under argon at 60° C. for 16 hours. The reaction mixture is then precipitated from 300 ml of hexane and the precipitate thus obtained is dried under vacuum to give the desired product in the form of a brittle yellow solid. This yellow solid is soluble at 25° C. to 50% by weight in solvents such as butyl acetate, and makes it possible to obtain a solution of polymer in a cosmetic solvent.

EXAMPLE 6

4.38 g of the polyester synthesized in step A of Example 4 are dissolved in 20 ml of chloroform in the presence of dibutyltin dilaurate. 0.87 g of the ureidopyrimidone represented below is added to the reaction medium:

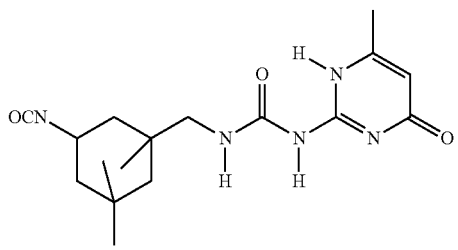

The mixture is stirred under argon at 60° C. for 16 hours. The reaction mixture is then precipitated from 150 ml of hexane, and the precipitate thus obtained is dried under vacuum to give the desired product in the form of a brittle yellow solid. This yellow solid is soluble at 25° C., to 50% by weight, in solvents such as butyl acetate, and makes it possible to obtain a solution of polymer in a cosmetic solvent.

EXAMPLE 7

A/

90 g of benzoic acid, 160 g of isostearic acid and 130 g of pentaerythritol are introduced into a 0.5 liter reactor. The reactor is maintained under an argon atmosphere throughout the synthesis (sparging). The mixture is heated to 130° C. to obtain a homogeneous solution, and is then maintained at 180° C. for 1 hour. The temperature is increased to 230° C. until an acid number of less than or equal to 1 is obtained.

The temperature is reduced to 160° C., and 135 g of isophthalic acid are added, followed by heating to 230° C. After 4 hours, the polymerization kinetics are monitored by the acid number. When an acid number of less than 10 is obtained, the synthesis is stopped.

A polymer with an acid number of 8.0 and a hydroxyl number of 165 is obtained.

B/

12 g of the polyester synthesized above are dissolved in 50 ml of chloroform in the presence of dibutyltin dilaurate. 0.61 g of the ureidopyrimidone represented below is added to the reaction medium:

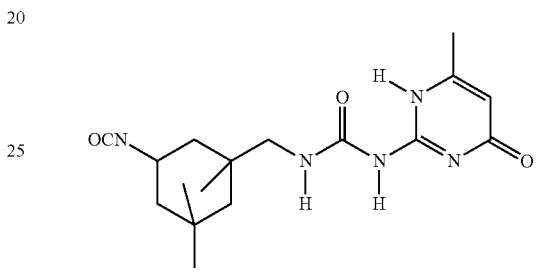

The mixture is stirred under argon at 60° C. for 16 hours. The reaction medium is then precipitated from 150 ml of hexane and the precipitate thus obtained is dried under vacuum to give the desired product in the form of a brittle yellow solid.

EXAMPLE 8

10.5 g of the polyester synthesized in step A of Example 7 are dissolved in 50 ml of chloroform in the presence of dibutyltin dilaurate. 1.07 g of the ureidopyrimidone represented below are added to the reaction medium:

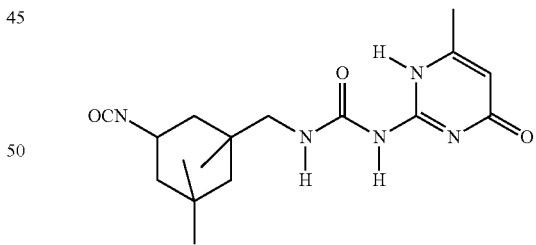

The mixture is stirred under argon at 60° C. for 16 hours. The reaction medium is then precipitated from 150 ml of hexane and the precipitate thus obtained is dried under vacuum to give the desired product in the form of a brittle yellow solid.

EXAMPLE 9

A lipstick is prepared, comprising:
15% polyethylene wax
30% polymer prepared in Example 1
50% isoparaffin
5% DC Red 7 pigment

EXAMPLE 10

A gloss is prepared, comprising:
30% polybutene (95/5 monoolefins/isoparaffins, MW 2060)
35% polybutene (monoolefins/isoparaffins MW=920)
30% polymer prepared in Example 1
5% DC Red 7 pigment.

EXAMPLE 11

A nail varnish is prepared, comprising (weight %):

| | |
|---|---|
| Nitrocellulose | 15% |
| Polymer of Example 6 | 9% |
| Tributyl acetyl citrate | 5% |
| Pigments | 1% |
| Hectorite | 1.2% |
| Isopropyl alcohol | 8% |
| Ethyl acetate, butyl acetate | qs 100% |

The invention claimed is:

1. A cosmetic or dermatological composition comprising, in a cosmetically or dermatologically acceptable medium, a polycondensate polymer comprising:
    (a) a polymer backbone obtained by a process comprising reacting:
        from 10% to 60% by weight, relative to the total weight of the said backbone, of at least one polyol comprising 3 to 6 hydroxyl groups;
        from 0.1% to 80% by weight, relative to the total weight of the said backbone, of at least one monocarboxylic acid containing 6 to 32 carbon atoms;
        from 5% to 60% by weight, relative to the total weight of the said backbone, of at least one polycarboxylic acid comprising at least two carboxylic groups, and/or a cyclic anhydride of such a polycarboxylic acid and/or a lactone comprising at least one carboxylic group; and
    (b) at least one junction group linked to the polymer backbone by a urethane group and capable of establishing H bonds with one or more partner junction groups, each pairing of a junction group involving at least three H bonds, wherein the junction group has the formula A or B, wherein
    A has the structure:

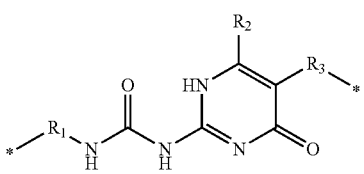

wherein
    R1 and R3, are independently, a divalent carbon-based radical selected from the group consisting of (i) a linear or branched $C_1$-$C_{30}$ alkyl group, (ii) a $C_4$-$C_{12}$ cycloalkyl group and (iii) a $C_4$-$C_{12}$ aryl group; optionally comprising 1 to 8 heteroatoms selected from the group consisting of O, N, S, F, Si and P; and optionally substituted with an ester or amide function or with a $C_1$-$C_{12}$ alkyl radical; or a mixture of these groups;
    R2 is H, Br, Cl, F or a linear, branched or cyclic, saturated or unsaturated, optionally aromatic $C_1$-$C_{32}$ monovalent hydrocarbon-based group, optionally comprising one or more heteroatoms selected from the group consisting of O, S, N, P and F, and
B has the structure:

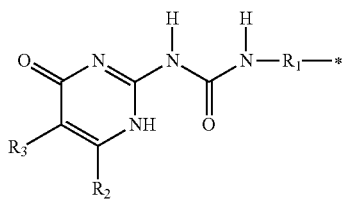

wherein
    R1 is a divalent carbon-based group selected from the group consisting of (i) a linear or branched $C_1$-$C_{30}$ alkyl group, (ii) a $C_4$-$C_{12}$ cycloalkyl group and (iii) a $C_4$-$C_{12}$ aryl group; comprising 1 to 8 heteroatoms selected from the group consisting of O, N, S, F, Si and P; and/or optionally substituted with an ester or amide function or with a $C_1$-$C_{12}$ alkyl radical; or a mixture of these groups; and
    R2 and R3, are independently, a hydrogen atom or a linear, branched or cyclic, saturated or unsaturated $C_1$-$C_{32}$ carbon-based(alkyl), radical, optionally comprising one or more heteroatoms selected from the group consisting of O, N, S, F, Si and P.

2. The composition according to claim 1, wherein the monocarboxylic acid is at least one selected from the group consisting of a saturated monocarboxylic acid, a non-aromatic unsaturated monocarboxylic acid, a conjugated acid and an aromatic monocarboxylic acid.

3. The composition according to claim 1, wherein the polycarboxylic acid or the cyclic anhydride thereof is at least one selected from the group consisting of a linear, branched and/or cyclic, saturated or unsaturated, or aromatic, polycarboxylic acid containing 2 to 50 carbon atoms;
    comprising:
    at least two carboxylic groups;
    optionally 1 to 10 identical or different heteroatoms selected from the group consisting of O, N and S; and/or optionally at least one —$CF_2$— or —$CF_3$ perfluoro radical; and anhydrides thereof;
    a polycarboxylic acid with a saturated or unsaturated, linear or branched chain comprising:
    at least one heteroatom selected from the group consisting of O, N and S,
    at least one perfluoro radical —$CF_2$— or —$CF_3$ and
    at least two carboxylic groups; and anhydrides thereof;
    a saturated, unsaturated, or aromatic, heterocyclic polycarboxylic acid, comprising:
    at least one heteroatom selected from the group consisting of O, N and/or S, and
    at least two carboxylic groups; and anhydrides thereof;
    a sugar-based polycarboxylic acid obtained by oxidation of an aldose, and comprising at least two carboxylic groups COOH; and anhydrides thereof;
    itaconic anhydride; 1,4,5,8-naphthalenetetracarboxylic acid 1,4-monoanhydride; and
    a polycarboxylic or heterocyclic amino acid, comprising:
    a saturated or unsaturated, linear, branched and/or cyclic chain,
    optionally at least one heteroatom selected from the group consisting of O, N and/or S, optionally at least one perfluoro radical —$CF_2$— or —$CF_3$; at least one primary, secondary or tertiary amine function and at least two carboxylic groups; and anhydrides thereof.

4. The composition according to claim 1, wherein the at least one polycarboxylic acid, or the anhydride thereof, is selected from the group consisting of decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid fatty acid dimers cyclohexanetricarboxylic acid, trimellitic acid, 1,2,3-benzenetricarboxylic acid, 1,3,5-benzenetricarboxylic acid butanetetracarboxylic acid, and pyromellitic acid,
2,2'-[1,5-pentanediylbis(thio)]bis-acetic acid,
6,6'-[(1,2-dioxo-1,2-ethanediyl)diimino]bis-hexanoic acid,
2,2'-sulfinylbis-acetic acid, 4,13-dioxo-3,5,12,14-tetraazahexadecanedioic acid,
poly(ethylene glycol)disuccinate, having a mass of 250-600,
poly(ethylene glycol)bis(carboxymethyl) ether, having a mass of 250-600,
poly[oxy(1,2-dicarboxy-1,2-ethanediyl)], having a DP<10,
8-[(carboxymethyl)amino]-8-oxooctanoic acid,
2,2'-[methylenebis(sulfonyl)]bis-acetic acid,
4,4'-(1,6-hexanediyldiimino)bis[4-oxobutanoic acid],
4,9-dioxo-3,5,8,10-tetraazadodecanedioic acid,
4-[(1-carboxyethyl)amino]-4-oxobutanoic acid,
6-[(3-carboxy-1-oxopropyl)amino]hexanoic acid,
N,N'-(1,6-dioxo-1,6-hexanediyl)bis-glycine,
N,N'-(1,6-dioxo-1,6-hexanediyl)bis-phenylalanine,
N,N'-(1,3-dioxo-1,3-propanediyl)bis-glycine,
4,4'-[(1,4-dioxo-1,4-butanediyl)diimino]bis-butanoic acid,
4,4'-[(1,6-dioxo-1,6-hexanediyl)diimino]bis-butanoic acid,
6,6'-[1,6-hexanediylbis(iminocarbonylimino)]bis-hexanoic acid,
N-benzoyl-S-(carboxymethyl)cysteine,
N,N'-(2,2,3,3-tetrafluoro-1,4-dioxo-1,4-butanediyl)bisglycine,
N,N'-(2,2,3,3-tetrafluoro-1,4-dioxo-1,4-butanediyl)bisalanine,
4,4'-[(2,2,3,3-tetrafluoro-1,4-dioxo-1,4-butanoic acid,
N,N'-(1,5-dioxo-1,5-pentanediyl)bis-glycine,
N,N'-(1,9-dioxo-1,9-nonanediyl)bis-glycine,
N,N'-(1,10-dioxo-1,10-decanediyl)bis[N-methyl]glycine,
bis(3-carboxypropyl) ester of propanedioic acid,
7,16-dioxo-6,8,15,17-tetraazadocosanedioic acid,
N-benzoyl-N-(2-carboxyethyl)glycine,
[2-[(2-carboxymethyl)amino]-2-oxoethyl]benzenepropanoic acid,
[2-[(2-carboxyethyl)amino]-2-oxoethyl]benzenepropanoic acid,
4,7,9,12-tetraoxapentadecanedioic acid,
2,3-pyridinedicarboxylic acid, 4-pyranone-2,6-dicarboxylic acid,
2,5-pyrazinedicarboxylic acid,
2,5-pyridinedicarboxylic acid,
2,3-benzofurandicarboxylic acid,
7-oxabicyclo[2.2.1]heptane-2,3-dicarboxylic acid,
3,4-pyridinedicarboxylic acid,
2,4-pyridinedicarboxylic acid,
3,5-pyridinedicarboxylic acid,
2,6-pyridinedicarboxylic acid,
1H-imidazole-4,5-dicarboxylic acid, 2,3-quinolinedicarboxylic acid,
6,6,7,7-tetrafluoro-3-oxabicyclo[3.2.0]heptane-2,4-dicarboxylic acid,
2,6-pyrazinedicarboxylic acid,
2,6-dimethyl-3,5-pyridinedicarboxylic acid,
1-phenyl-1H-pyrazole-3,4-dicarboxylic acid,
2,5-furandicarboxylic acid,
3,4-furandicarboxylic acid,
1,2,5-thiadiazole-3,4-dicarboxylic acid,
1,4-dihydro-1,2,4,5-tetrazine-3,6-dicarboxylic acid,
2,3-furandicarboxylic acid,
3,4-thiophenedicarboxylic acid,
1H-1,2,3-triazole-4,5-dicarboxylic acid,
2-methylimidazole-4,5-dicarboxylic acid,
2,4-quinolinedicarboxylic acid, -naphtho[2,1-b]furan-1,2-dicarboxylic acid,
3,4-quinolinedicarboxylic acid,
7-oxabicyclo[2.2.1]hept-5-ene-2,3-dicarboxylic acid,
2,3-quinoxalinedicarboxylic acid,
1,4-piperazinedicarboxylic acid,
2,5-dimethyl-3,4-furandicarboxylic acid,
tetrahydro-2,5-thiophenedicarboxylic acid,
4-phenyl-3,5-pyridinedicarboxylic acid,
thieno[3,2-b]thiophene-2,5-dicarboxylic acid,
3-methyl-2,4-thiophenedicarboxylic acid,
naphthostyril-5,6-dicarboxylic acid,
3-phenyl-2,4-quinolinedicarboxylic acid,
3,4-dimethyl-2,5-dicarboxythiophene,
3,4-diphenyl-2,5-thiophenedicarboxylic acid, 2,5-diphenyl-3,4-furandicarboxylic acid,
7-oxo-7H-benzimidazo[2,1-a]benz[de]isoquinoline-3,4-dicarboxylic acid,
2,3-dihydro-1,3-dioxo-1H-benz[de]isoquinoline-6,7-dicarboxylic acid,
3,4-bis(phenylmethoxy)-2,5-furandicarboxylic acid,
4,4'-bibenzoic acid-2,2'-sulfone,
2,7-diphenyl-m-anthrazoline-4,5-dicarboxylic acid,
2,4-pyrimidinedicarboxylic acid,
2-phenyl-4,5-thiazoledicarboxylic acid,
6-phenyl-2,3-pyridinedicarboxylic acid,
5,6-dimethyl-2,3-pyrazinedicarboxylic acid,
3,7-dibenzothiophenedicarboxylic acid,
9-oxo-9H-xanthene-1,7-dicarboxylic acid,
2-(1,1-dimethylethyl)-H-imidazole-4,5-dicarboxylic acid,
6,7-quinolinedicarboxylic acid,
6-methyl-2,3-pyridinedicarboxylic acid,
4,5-pyrimidinedicarboxylic acid, 2-methyl-3,4-furandicarboxylic acid,
1,2-indolizinedicarboxylic acid,
2,8-dibenzothiophenedicarboxylic acid,
3,6-pyridazinedicarboxylic acid,
1,10-phenanthroline-2,9-dicarboxylic acid,
1,4,5,6-tetrahydro-5,6-dioxo-2,3-pyrazinedicarboxylic acid,
3,4-dimethoxy-2,5-furandicarboxylic acid,
2-ethyl-4,5-imidazoledicarboxylic acid,
2-propyl-1H-imidazole-4,5-dicarboxylic acid,
4-phenyl-2,5-pyridinedicarboxylic acid,
4,5-pyridazinedicarboxylic acid,
1,4,5,8-tetrahydro-1,4:5,8-diepoxynaphthalene-4a,8a-dicarboxylic acid,
5,5-dioxide-2,8-dibenzothiophenedicarboxylic acid, pyrazolo[1,5-a]pyridine-2,3-dicarboxylic acid,
2,3-dihydro-1H-pyrrolizine-1,7-dicarboxylic acid,
6-methyl-2,4,5-pyridinetricarboxylic acid,
pyrrolo[2,1,5-cd]indolizine-5,6-dicarboxylic acid,
3,4-bis(2,2,3,3,4,4,4-heptafluorobutyl)-1H-pyrrole-2,5-dicarboxylic acid,
6,7,9,10,17,18,20,21-octahydrodibenzo[b,k][1,4,7,10,13,16]hexaoxacyclooctadecin-2,14-dicarboxylic acid,
6,7,9,10,17,18,20,21-octahydrodibenzo[b,k][1,4,7,10,13,16]hexaoxacyclooctadecin-2,13-dicarboxylic acid,
2-methyl-3,4-quinolinedicarboxylic acid,
4,7-quinolinedicarboxylic acid,
3,5-isoxazoledicarboxylic acid,
2-(trifluoromethyl)-3,4-furandicarboxylic acid,
5-(trifluoromethyl)-2,4-furandicarboxylic acid,
6-methyl-2,4-quinolinedicarboxylic acid,
5-oxo-1,2-pyrrolidinedicarboxylic acid,
5-ethyl-2,3-pyridinedicarboxylic acid,
1,2-dihydro-2-oxo-3,4-quinolinedicarboxylic acid,
4,6-phenoxathiindicarboxylic acid,
10,10-dioxide 1,9-phenoxathiindicarboxylic acid,
3,4-dihydro-2H-1,4-thiazine-3,5-dicarboxylic acid,
2,7-di(tert-butyl)-9,9-dimethyl-4,5-xanthenedicarboxylic acid,
6-methyl-2,3-quinoxalinedicarboxylic acid,
3,7-quinolinedicarboxylic acid,
2,5-quinolinedicarboxylic acid,
2-methyl-6-phenyl-3,4-pyridinedicarboxylic acid,
3,4-dimethylthieno[2,3-b]thiophene-2,5-dicarboxylic acid,
3,4-dimethoxythiophene-2,5-dicarboxylic acid,
5-methyl-3,4-isoxazoledicarboxylic acid,
2,6-bis(aminocarbonyl)-3,5-pyridinedicarboxylic acid,
3,5-bis(aminocarbonyl)-2,6-pyrazinedicarboxylic acid,
2,3-pyridinedicarboxylic acid,
6-(1,1-dimethylethyl)-2-ethyl-3,4-pyridinedicarboxylic acid,
3-methyl-5-phenyl-2,4-thiophenedicarboxylic acid,
1,2-dihydro-2-oxo-6-phenyl-3,5-pyridinedicarboxylic acid,
8-methyl-2,4-quinolinedicarboxylic acid,
4-ethyl-2,6-dimethyl-3,5-pyridinedicarboxylic acid,
5-(phenoxymethyl)-2,4-furandicarboxylic acid,
5-(acetylamino)-3-methyl-2,4-thiophenedicarboxylic acid,
2-(4-heptylphenyl)-4,8-quinolinedicarboxylic acid,
2,8-bis(4-heptylphenyl)pyrido[3,2-g]quinoline-4,6-dicarboxylic acid,
1,2,3,4,6,7,8,9-octahydro-2,8-dioxopyrido[3,2]quinoline-3,7-dicarboxylic acid,
2,8-dimethylpyrido[3,2-g]quinoline-3,7-dicarboxylic acid,
5,6-quinolinedicarboxylic acid,
6-ethyl-2-methylcinchomeronic acid,
2-methyl-6-propylcinchomeronic acid,
6-isopropyl-2-methylcinchomeronic acid,
6-tert-butyl-2-methylcinchomeronic acid,
1,4-dimethyl-7-oxabicyclo[2.2.1]heptane-2,3-dicarboxylic acid,
1,2-dihydro-2-oxo-3,8-quinolinedicarboxylic acid,
1,2-dihydro-2-oxo-3,6-quinolinedicarboxylic acid,
1,2-dihydro-2-oxo-3,7-quinolinedicarboxylic acid,
3,7-dimethyl-2,8-diphenylpyrido[3,2-g]quinoline-4,6-dicarboxylic acid,
8-methyl-2,3-quinolinedicarboxylic acid,
3-[[(1,1-dimethylethyl)amino]sulfonyl]-2,5-thiophenedicarboxylic acid,
4-(acetylamino)-2,3-thiophenedicarboxylic acid,
2,5-pyridinedicarboxylic acid,
2,6-pyridinedicarboxylic acid,
2,4-thiophenedicarboxylic acid,
2,5-thiophenedicarboxylic acid,
1,4-pyran-2,6-dicarboxylic acid,
ribaric acid,
glucaric acid,
xylaric acid,
arabinaric acid,
mannaric acid,
idaric acid,
altraric acid,
L-glucaric acid,
L-arabinaric acid,
allaric acid,
galactaric acid,
meso-tartaric acid,
D-glucaric acid,
L-idaric acid,
hexaric acid,
2,3-dihydroxybutanedioic acid,
D-tartaric acid,
D,L-tartaric acid,
D-glucaric acid,
tartaric acid,
tetrahydroxysuccinic acid,
2-carboxy-2,3-dideoxy-D-manno-2-octulopyranosonic acid,
methyl-3-deoxy-D-arabino-2-heptulopyranosaric acid,
D-lyxo-2-heptulopyranosaric acid,
2,6-anhydro-L-glycero-L-galactoheptaric acid,
1,4-dihydro-4-oxo-2,6-pyridinedicarboxylic acid,
2,6-piperidinedicarboxylic acid,
1H-pyrrole-3,4-dicarboxylic acid,
4-amino-2,6-dicarboxylic acid,
1-methyl-1H-pyrazole-3,4-dicarboxylic acid,
2,3-piperidinedicarboxylic acid,
1-methyl-1H-imidazole-4,5-dicarboxylic acid,
2,4-thiazolidinedicarboxylic acid,
1-(phenylmethyl)-1H-imidazole-4,5-dicarboxylic acid,
5-amino-6-oxo-2,3-piperidinedicarboxylic acid,
5-amino-6-oxo-2,4-piperidinedicarboxylic acid,
5-amino-6-oxo-2,3-piperidinedicarboxylic acid,
5-amino-6-oxo[2S-(2α,4β,5α)]-2,4-piperidinedicarboxylic acid,
(2S,4R)-2,4-pyrrolidinedicarboxylic acid,
(2S-cis)-2,4-pyrrolidinedicarboxylic acid,
2-amino-1H-imidazole-4,5-dicarboxylic acid,
2,5-pyrrolidinedicarboxylic acid,
4-amino-3,5-isothiazoledicarboxylic acid,
1-methyl-1H-pyrazole-3,5-dicarboxylic acid,
7-(diethylamino)-2-oxo-2H-1-benzopyran-3,4-dicarboxylic acid,
3,4-diethyl-1H-pyrrole-2,5-dicarboxylic acid,
1-phenyl-1H-pyrrole-3,4-dicarboxylic acid,
cis-2,3-piperazinedicarboxylic acid,
2,3-piperazinedicarboxylic acid,
2,5-piperazinedicarboxylic acid,
2,6-piperazinedicarboxylic acid,
2-amino-3,5-pyridinedicarboxylic acid,
2-methylpyrrole-3,4-dicarboxylic acid,
4-(methylamino)-2,6-pyridinedicarboxylic acid,
2-amino-6-methyl-3,4-pyridinedicarboxylic acid,
5-amino-2-methyl-3,4-pyridinedicarboxylic acid,
2-amino-6-methyl-3,5-pyridinedicarboxylic acid,
2,5-dimethylpyrrole-3,4-dicarboxylic acid, 2,5-dimethylpyrrole-3,4-dicarboxylic acid,
2-amino-6-hydroxy-3,5-pyridinedicarboxylic acid,
2,4-pyrrolidinedicarboxylic acid,
1H-indole-2,4-dicarboxylic acid,
1H-indole-2,6-dicarboxylic acid,
1H-indole-2,5-dicarboxylic acid,
5-phenyl-2,4-pyrrolidinedicarboxylic acid,
5-methyl-2,4-pyrrolidinedicarboxylic acid,
trans-2,4-azetidinedicarboxylic acid,
cis-2,4-azetidinedicarboxylic acid,
3,5-piperidinedicarboxylic acid,
2,3-pyrrolidinedicarboxylic acid,
2,3-azetidinedicarboxylic acid,
3,4-pyrrolidinedicarboxylic acid,
2,3-dihydro-6H-1,4-dioxino[2,3-c]pyrrole-5,7-dicarboxylic acid,
1H-imidazole-2,4-dicarboxylic acid,
1-butyl-1H-pyrrole-2,3-dicarboxylic acid,
3-amino-1-oxide-2,4-pyridinedicarboxylic acid,
2,3-dihydro-5-phenyl-1H-pyrrolizine-6,7-dicarboxylic acid,
3a,4,5,9b-tetrahydro-3H-cyclopenta[c]quinoline-4,6-dicarboxylic acid,
3a,4,5,9b-tetrahydro-3H-cyclopenta[c]quinoline-4,8-dicarboxylic acid,
2,3-dihydro-1H-imidazole-4,5-dicarboxylic acid,
5-amino-6-methyllutidinic acid,
1H-indole-3,7-dicarboxylic acid,
3,3-dimethyl-2,6-piperidinedicarboxylic acid,
1-butyl-2,5-pyrrolidinedicarboxylic acid,
1H-indole-4,6-dicarboxylic acid,
1-(phenylmethyl)-3,4-pyrrolidinedicarboxylic acid,
3-(carboxymethyl)-1H-indole-2,6-dicarboxylic acid,
3,4-bis(2,2,2-trifluoroethyl)-1H-pyrrole-2,5-dicarboxylic acid,
9-hexyl-9H-carbazole-3,6-dicarboxylic acid,
3-methyl-5-(1-piperazinylsulfonyl)-2,4-thiophenedicarboxylic acid,
2,3,4,9-tetrahydro-1H-carbazole-5,7-dicarboxylic acid,
2,3-dimethyl-1H-indole-4,6-dicarboxylic acid,
7-amino-1,4-dihydro-4-oxo-3,6-quinolinedicarboxylic acid,
5-amino-3-methyl-2,4-thiophenedicarboxylic acid,
(m-tolylimino)diacetic acid,
(o-tolylimino)diacetic acid,
D-cystathionine,
phenethyliminodiacetic acid,
2-benzyl-2,2'-iminodiacetic acid,
L-α-glutamyl-L-alanyl-L-alanine,
N,N'-dibenzylethylenediaminediacetic acid,
N-L-γ-glutamyl-D-alanine,
glycyl-L-glutamylglycine,
N-(carboxymethyl)-N-(tetrahydro-1,1-dioxido-3-thienyl)glycine,
N-(2-carboxyethyl)-N-phenyl-beta-alanine,
N-(carboxymethyl)-N-octylglycine,
N-(tert-butoxycarbonyl)iminodiacetic acid,
N-(carboxymethyl)-L-alanine,
N-(6-aminohexyl)-N-(carboxymethyl)glycine,
N-(carboxymethyl)-N-tetradecylglycine,
N-(1-carboxyethyl)-D-alanine,
N-(carboxymethyl)-D-alanine,
decyliminodiacetic acid,
3,3'-(dimethylhydrazono)bis-propanoic acid,
N-(carboxymethyl)-N-[2-(2,6-dioxo-4-morpholinyl)ethyl]glycine,
N-alpha-aspartylglycine,
N-beta-aspartylglycine,
N-L-alpha-aspartyl-beta-alanine,
3,4-xylylamino-N,N-diacetic acid,
N-(1-carboxyethyl)alanine,
N-(carboxymethyl)alanine,
N,N'-methylenebis-glycine,
N-(aminomethyl)-N-(carboxymethyl)glycine,
N-(aminomethyl)-N-(carboxymethyl)glycine,
2,2'-(methylhydrazono)bis-acetic acid,
N-(2-carboxyethyl)-N-(4-methylphenyl)-beta-alanine,
N-(2-carboxyethyl)-N-(3-methylphenyl)-beta-alanine,
3-[(carboxymethyl)amino]alanine,
D-alpha-aspartyl-D-alanine,
N-(2-carboxyethyl)-N-(1-oxohexadecyl)-beta-alanine,
N-(2-carboxyethyl)-N-(1-oxodecyl)-beta-alanine,
N-(2-carboxyethyl)-N-(1-oxotetradecyl)-beta-alanine,
amino[(carboxymethyl)thio]acetic acid,
N,N'-1,6-hexanediylbis-beta-alanine,
N-(carboxymethyl)-N-phenyl-beta-alanine,
N-(1-carboxyethyl)-L-alanine,
L-glutamic acid,
L-aspartic acid,
3,3',3''-[1,2,3-propanetriyltris(oxy)]tris-propanoic acid,
pyrazinetricarboxylic acid,
4-(3-carboxyphenyl)-2,5-pyridinedicarboxylic acid,
3-(carboxymethyl)-2,4-quinolinedicarboxylic acid,
3-(carboxymethyl)-1H-indole-2,5-dicarboxylic acid,
3-C-carboxy-2-deoxy-D-threo-pentaric acid,
hydroxycitric acid,
D-glucopyranuronosyl-D-arabino-2-hexulofuranosidaric acid,
2,3,5,6-pyridinetetracarboxylic acid,
N,N-1,2-ethanediylbis[N-(carboxymethyl)-β-alanine,
L-α-aspartyl-L-aspartic acid,
4-[bis(carboxymethyl)amino]benzoic acid,
7-[bis(carboxymethyl)amino]heptanoic acid,
N-(2-carboxyethyl)aspartic acid,
3-[bis(2-carboxyethyl)amino]benzoic acid and
4-[bis(2-carboxyethyl)amino]benzoic acid;
and the cyclic anhydrides of these acids.

5. The composition according to claim 1, wherein the lactone is at least one selected from the group consisting of
tetrahydro-2,2-dimethyl-5-oxo-3-furancarboxylic acid,
4,7,7-trimethyl-3-oxo-2-oxabicyclo[2.2.1]heptane-1-carboxylic acid,
4,6-dimethyl-2-oxo-2H-pyran-5-carboxylic acid,
2-oxo-2H-pyran-5-carboxylic-2-pentenedioic acid,
2-oxo-2H-1-benzopyran-3-carboxylic acid,
2-oxo-2H-pyran-6-carboxylic acid,
1,3-dihydro-3-oxo-1-isobenzofurancarboxylic acid,
4-methyl-2-oxo-2H-1-benzopyran-3-carboxylic acid,
1-oxo-1H-2-benzopyran-3-carboxylic acid,
8-methoxy-2-oxo-2H-1-benzopyran-3-carboxylic acid,
2-oxo-1-oxaspiro[4.5]decane-4-carboxylic acid,
2-oxo-2H-pyran-3-carboxylic acid,
4-methyl-2-oxo-2H-pyran-6-carboxylic acid,
3-oxo-3H-naphtho[2,1-b]pyran-2-carboxylic acid,
tetrahydro-5-oxo-2,3-furandicarboxylic acid,
1,3-dihydro-3-oxo-4-isobenzofurancarboxylic acid,
1,3-dihydro-1-oxo-5-isobenzofurancarboxylic acid,
hexahydro-2-oxo-3,5-methano-2H-cyclopenta[b]furan-7-carboxylic acid,
6-methyl-2,4-dioxo-2H-pyran-5-carboxylic acid,
1-oxo-3-isochromancarboxylic acid,
2-oxo-2H-1-benzopyran-6-carboxylic acid,
6-methyl-2-oxo-2H-1-benzopyran-3-carboxylic acid, 2,5-dihydro-4,5,5-trimethyl-2-oxo-3-furancarboxylic acid,
tetrahydro-5-oxo-2-phenyl-3-furancarboxylic acid,
tetrahydro-5-oxo-4-propyl-2-furoic acid,
2-butyl-2,3-dideoxypentaric acid,
2-oxo-2H-1-benzopyran-7-carboxylic acid,
2-oxo-1-oxaspiro[4.4]nonane-4-carboxylic acid,
4-ethyltetrahydro-5-oxo-2-furoic acid,
5-ethyltetrahydro-2,3-dimethyl-6-oxo-2H-pyran-2-carboxylic acid,
7-methoxy-2-oxo-2H-1-benzopyran-3-carboxylic acid,
2-oxo-2H-1-benzopyran-4-carboxylic acid,
2-oxo-6-pentyl-2H-pyran-3-carboxylic acid,
7-oxo-4-oxepanecarboxylic acid,
3-(carboxymethyl)-2,3-dideoxypentaric acid,
2,3-dihydro-2-oxo-7-benzofurancarboxylic acid,
1,3,4,5-tetrahydro-1-oxo-2-benzoxepin-7-carboxylic acid,
3,4-dihydro-3-oxo-1H-2-benzopyran-6-carboxylic acid,
2,3,4,5-tetrahydro-2-oxo-1-benzoxepin-7-carboxylic acid,
3,4-dihydro-1-oxo-1H-2-benzopyran-8-carboxylic acid,
1,3,4,5-tetrahydro-3-oxo-2-benzoxepin-9-carboxylic acid,
1,3,4,5-tetrahydro-3-oxo-2-benzoxepin-7-carboxylic acid,
3,4-dihydro-2-oxo-2H-1-benzopyran-8-carboxylic acid,
1,3,4,5-tetrahydro-1-oxo-2-benzoxepin-9-carboxylic acid,
3,4-dihydro-1-oxo-1H-2-benzopyran-6-carboxylic acid,
3,4-dihydro-3-oxo-1H-2-benzopyran-8-carboxylic acid,
2,3,4,5-tetrahydro-2-oxo-1-benzoxepin-9-carboxylic acid,
isocitric acid lactone and
5-oxo-2-tetrahydrofurancarboxylic acid.

6. The composition according to claim 1, wherein the junction group comprises the group having the structure of formula (B):

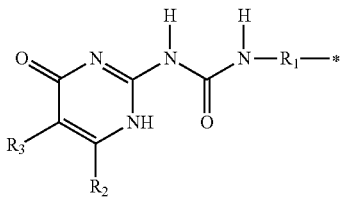

wherein
R1 is a divalent carbon-based group selected from the group consisting of (i) a linear or branched $C_1$-$C_{30}$ alkyl group, (ii) a $C_4$-$C_{12}$ cycloalkyl group and (iii) a $C_4$-$C_{12}$ aryl group; optionally comprising 1 to 8 heteroatoms selected from the group consisting of O, N, S, F, Si and P; and/or optionally substituted with an ester or amide function or with a $C_1$-$C_{12}$ alkyl radical; or a mixture of these groups; and
R2 and R3, are independently, a hydrogen atom or a linear, branched or cyclic, saturated or unsaturated $C_1$-$C_{32}$ carbon-based(alkyl), radical, optionally comprising one or more heteroatoms selected from the group consisting of O, N, S, F, Si and P.

7. The composition according to claim 1, wherein
A is
a linear or branched $C_1$-$C_{30}$ alkyl group or a $C_4$-$C_{12}$ cycloalkyl group or a $C_4$-$C_{12}$ aryl group; optionally substituted with an ester and/or amide function; having a structure —$(CH_2)_c$—, —$(CHR)_c$— or —$(CRR')_c$—,
wherein
R and R', are independently a linear or branched $C_1$-$C_{30}$ alkyl group and c is an integer between 1 and 30; or
A has the structure:

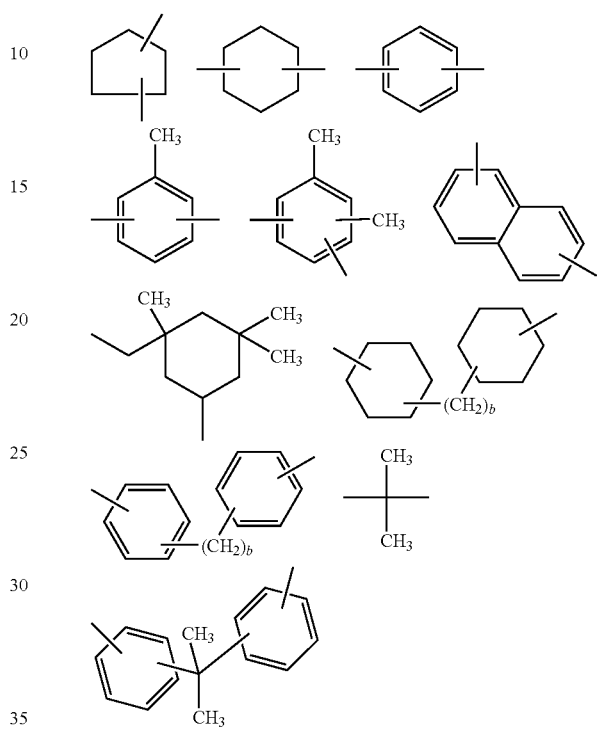

wherein b is an integer between 1 and 3; and also
any combination of these structures.

8. The composition according to claim 1, wherein A has the structure:

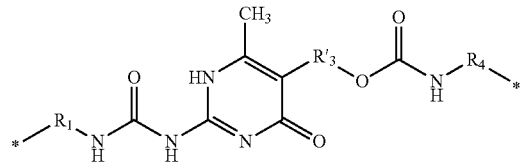

wherein
R1, R3 and R4, independently of each other, are selected from the group consisting of methylene, 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene), 1,7-(3,7-dimethyloctylene), 4,4'-methylenebiscyclohexylene, 2-methyl-1,3-phenylene, 4-methyl-1,3-phenylene, 4,4'-biphenylenemethylene, 1,2-tolylene, 1,4-tolylene, 2,4-tolylene, 2,6-tolylene, 1,5-naphthylene, 4,4'-methylenebis(phenyl), tetramethylxylylene, and a divalent radical of isophorone.

9. The composition according to claim 1, wherein the junction group is derived from a compound selected from the group consisting of
1,4-diisocyanatobutane, 1,6-hexamethylene diisocyanate, 1,6-diisocyanatohexane, 1,5-diisocyanato-2-methylpentane, 1,4-diisocyanato-4-methylpentane, 1,6-diisocyanato-2,2,4-trimethylhexane, 1,6-diisocyanato-2,4,4-trimethylhexane, 1,5-diisocyanato-5-methylhexane, 3(4)-isocyanatomethyl-1-methylcyclohexyl isocyanate, 1,6-diisocyanato-6-methylheptane, 1,5-diisocyanato-2,2,5-trimethylhexane, 1,7-diisocyanato-3,7-dimethyloctane, 1-isocyanato-1,2,2-trimethyl-3-(2-isocyanatoethyl)cyclopentane, 1-isocyanato-n-butyl-3-(4-isocyanatobut-1-yl)cyclopentane, 1-isocyanato-1,2-dimethyl-3-ethyl-3-isocyanatomethylcyclopentane, 1-isocyanato-1-methyl-4-(4-isocyanatobut-2-yl)cyclohexane, 1-isocyanato-1,4-dimethyl-4-isocyanatomethylcyclohexane, 1-isocyanato-1,3-dimethyl-3-isocyanatomethylcyclohexane, 1,3-bis(isocyanatomethyl)cyclohexane, isophorone diisocyanate, 4,4'-methylenebis(cyclohexyl isocyanate), 1,4-diphenylene diisocyanate, tolylene 2,4-diisocyanate, tolylene 2,6-diisocyanate, 1,3-bis(isocyanatomethyl)benzene, 4,4'-methylenebis(phenyl isocyanate), naphthalene diisocyanate and tetramethyl-1,3-xylylenediisocyanate, which is bonded to the polymer backbone by a urethane group.

10. The composition according to claim 1, wherein A has the structure:

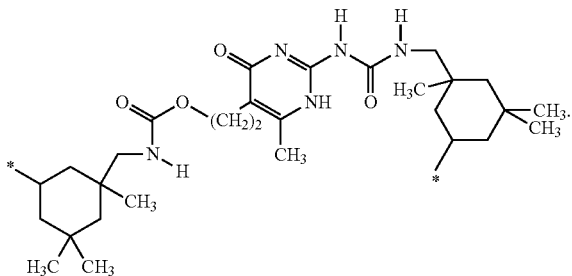

11. The composition according to claim 1, wherein B has the structure:

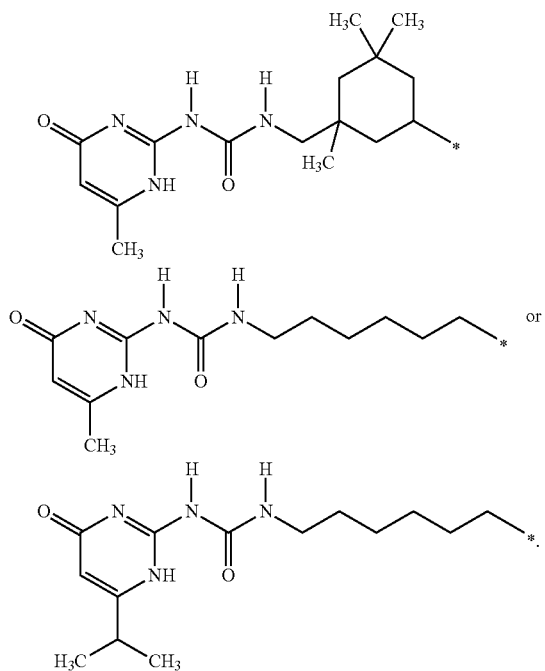

12. The composition according to claim 1, wherein an amount by weight of the polycondensate is between 0.1% and 80% by weight, relative to the weight of the final cosmetic or pharmaceutical composition.

13. The composition according to claim 1, wherein the cosmetically or dermatologically acceptable medium comprises at least one liquid fatty phase, which optionally comprises at least one compound selected from the group consisting of volatile or non-volatile carbon-based, hydrocarbon-based, fluoro and/or silicone oils, solvents of mineral, animal, plant or synthetic origin, and mixtures thereof.

14. The composition according to claim 1, wherein the cosmetically or dermatologically acceptable medium comprises at least one oil and/or one solvent selected from the group consisting of isododecane, hydrogenated polyisobutene, isononyl isononanoate, octyldodecanol, phenyl trimethicone, $C_{12}$-$C_{15}$ alkyl benzoates, ethyl and butyl acetates, and decamethylcyclopentasiloxane (D5).

15. A product, comprising the composition according to claim 1 wherein the product is for one selected from the group consisting of caring for and/or making up bodily or facial skin, lips, eyelashes, eyebrows, hair, scalp or nails; an antisun or self-tanning product; a haircare product; a haircare dyeing product, conditioning and caring for hair.

16. A cosmetic process for treating keratin materials, comprising:
applying to the keratin materials a cosmetic composition as defined in claim 1.

17. The composition according to claim 1, wherein the polyol comprises at least one member selected from the group consisting of 1,2,4-butanetriol, 1,2,6-hexanetriol, trimethylolethane, trimethylolpropane, glycerol, pentaerythritol, erythritol, diglycerol, ditrimethylolpropane, xylitol, sorbitol, mannitol, dipentaerythritol and triglycerol.

18. The composition according to claim 1, wherein the polyol is pentaerythritol.

19. The composition according to claim 1, wherein the polyol is 12% to 40% by weight, relative to the total weight of the polycondensate forming the polymer backbone.

20. The composition according to claim 1, wherein the polyol is 10% to 25% by weight, relative to the total weight of the polycondensate forming the polymer backbone.

21. The composition according to claim 1, wherein the monocarboxylic acid comprises at least one member selected from the group consisting of benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid.

22. The composition according to claim 1, wherein the monocarboxylic acid is benzoic acid.

23. The composition according to claim 1, wherein the monocarboxylic acid comprises at least one member selected from the group consisting of caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid and 4-cyclohexylbutyric acid, caproleic acid, obtusilic acid, undecylenic acid, dodecylenic acid, linderic acid, myristoleic acid, physeteric acid, tsuzuic acid, palmitoleic acid, oleic acid, petroselinic acid, vaccenic acid, elaidic acid, gondoic acid, gadoleic acid, erucic acid, cetoleic acid, nervonic acid, oleic acid, linoleic acid, linolenic acid, arachidonic acid, rumenic acid, eicosapentaenoic acid and docosahexaenoic acid, stillinguic acid (10:2 2t,4c), rumenic acid (18:2 9c,11t), conjugated linoleic acid (18:2 10t,12c), conjugated linolenic acid (18:3 9c,11t, 15c), conjugated linolenic acid (18:3 6c,9c,11t) and alpha-eleostearic acid (18:3 9c,11t,13t).

24. The composition according to claim 1, wherein the monocarboxylic acid comprises at least one member selected from the group consisting of lauric acid, palmitic acid, stearic acid, isostearic acid, behenic acid, caproleic acid, obtusilic acid, undecylenic acid, dodecylenic acid, linderic acid, myristoleic acid, physeteric acid, tsuzuic acid, palmitoleic acid, oleic acid, linoleic acid, linolenic acid, arachidonic acid, isooctanoic acid, 2-ethylhexanoic acid, isooctanoic acid, isononanoic acid, stillinguic acid (10:2 2t,4c), rumenic acid (18:2 9c,11t), conjugated linoleic acid (18:2 10t,12c), conjugated linolenic acid (18:3 9c,11t,15c), conjugated linolenic acid (18:3 6c,9c,11t) and alpha-eleostearic acid (18:3 9c,11t, 13t).

25. The composition according to claim 1, wherein the monocarboxylic acid is a mixture of an aromatic monocarboxylic acid and of a non-aromatic monocarboxylic acid.

26. The composition according to claim 1, wherein the monocarboxylic acid is 1.5% to 60% by weight, relative to the total weight of the polycondensate forming the polymer backbone.

27. The composition according to claim 1, wherein the polycarboxylic acid or its anhydride is isophthalic acid or phthalic anhydride.

28. The composition according to claim 1, wherein the polycarboxylic acid and/or the cyclic anhydride and/or the lactone thereof is 10% to 40% by weight relative to the total weight of the polycondensate forming the polymer backbone.

\* \* \* \* \*

UNITED STATES PATENT AND TRADEMARK OFFICE
CERTIFICATE OF CORRECTION

PATENT NO.         : 8,968,711 B2                                  Page 1 of 1
APPLICATION NO.    : 12/679839
DATED              : March 3, 2015
INVENTOR(S)        : Sandrine Chodorowski-Kimmes et al.

It is certified that error appears in the above-identified patent and that said Letters Patent is hereby corrected as shown below:

Title page, After item (65)
Should read
--(60)   Provisional application No. 60/984,738 filed on November 2, 2007--.

Claims
In Column 33, Lines 15-17, Claim 4
"itaconic acid fatty acid dimers cyclohexanetricarboxylic acid, trimellitic acid, 1,2,3-benzenetricarboxylic acid, 1,3,5-benzenetricarboxylic acid butanetetracarboxylic acid, and pyromellitic acid,"

should read --itaconic acid and fatty acid dimers, cyclohexanetricarboxylic acid, trimellitic acid, 1,2,3-benzenetricarboxylic acid, 1,3,5-benzenetricarboxylic acid, butanetetracarboxylic acid, and pyromellitic acid,--.

Signed and Sealed this
Third Day of November, 2015

Michelle K. Lee
*Director of the United States Patent and Trademark Office*